United States Patent
Pfluecker et al.

(10) Patent No.: US 7,101,537 B2
(45) Date of Patent: Sep. 5, 2006

(54) TRICYCLIC QUINOXALINE AND QUINOLINE DERIVATIVES AS A UV FILTER

(75) Inventors: Frank Pfluecker, Darmstadt (DE); Michael Schwarz, Weiterstadt (DE); Volker Scholz, Darmstadt (DE); Hans Neunhoeffer, Muehital (DE)

(73) Assignee: Merck Patentgesellschaft, Darmstadt (DE)

( * ) Notice: Subject to any disclaimer, the term of this patent is extended or adjusted under 35 U.S.C. 154(b) by 121 days.

(21) Appl. No.: 10/471,101

(22) PCT Filed: Feb. 11, 2002

(86) PCT No.: PCT/EP02/01402

§ 371 (c)(1),
(2), (4) Date: Sep. 8, 2003

(87) PCT Pub. No.: WO02/072583

PCT Pub. Date: Sep. 19, 2002

(65) Prior Publication Data

US 2004/0102446 A1    May 27, 2004

(30) Foreign Application Priority Data

Mar. 9, 2001 (DE) ................. 101 11 728

(51) Int. Cl.
*A61K 8/00* (2006.01)
*A61K 8/18* (2006.01)
*A61K 8/49* (2006.01)
*A61Q 17/04* (2006.01)

(52) U.S. Cl. ........................ 424/59; 424/70.9

(58) Field of Classification Search ............ 424/59, 424/70.9
See application file for complete search history.

(56) References Cited

U.S. PATENT DOCUMENTS

| | | | |
|---|---|---|---|
| 2,888,346 A * | 5/1959 | Tulagin et al. ......... | 96/84 |
| 3,935,312 A | 1/1976 | Lunkenheimer et al. | |
| 4,022,777 A * | 5/1977 | Sam et al. .............. | 260/250 Q |
| 4,228,151 A * | 10/1980 | Lang et al. ............ | 424/60 |
| 5,501,850 A | 3/1996 | Stein et al. | |
| 5,929,093 A | 7/1999 | Pang et al. | |
| 6,217,856 B1 * | 4/2001 | Ehlis et al. ............. | 424/70.9 |
| 2003/0207886 A1 | 11/2003 | Plücker et al. | |

OTHER PUBLICATIONS

Schipper and Day, Imidazoles. I. Imidazo[b]quinoxalines' Journal of the American Chemical Society, vol. 73(12), pp. 5672-5675 (1951).*
Sircar and Pal, "Studies in Heterocylic Compounds. Part II." Journal of the Indian Chemical Society, vol. IX, pp. 527-532 (1932).*

* cited by examiner

*Primary Examiner*—James O. Wilson
*Assistant Examiner*—Zachary C. Tucker
(74) *Attorney, Agent, or Firm*—Millen, White, Zelano & Branigan, P.C.

(57) ABSTRACT

The invention relates to the use of quinoxaline derivatives of formula I, represented by formulas 1a and 1b, as photostable UV filters, in particular in cosmetic and pharmaceutical preparations for protecting the human epidermis or human hair against UV radiation, above all in the 280–400 nm range.

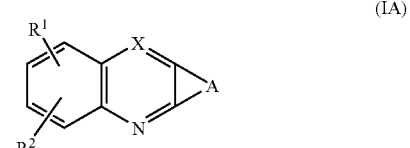

(IA)

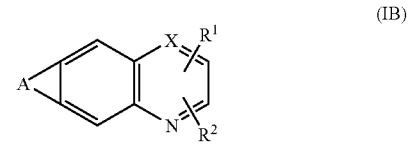

(IB)

15 Claims, No Drawings

TRICYCLIC QUINOXALINE AND QUINOLINE DERIVATIVES AS A UV FILTER

The invention relates to the use of quinoxaline derivatives as photostable UV filters in cosmetic and pharmaceutical preparations for protection of the human epidermis or human hair against UV radiation, especially in the range 280–400 m.

The light-protection agents employed in cosmetic and pharmaceutical preparations have the job of preventing or at least reducing the effects of harmful influences of sunlight on the human skin. In addition, however, these light-protection agents also serve to protect further ingredients against destruction or degradation by UV radiation. In hair-cosmetic preparations, the aim is to prevent damage to the keratin fibres by UV rays.

As is known, the skin reacts sensitively to solar radiation, which can cause normal sunburn or erythema, but also various degrees of burning.

However, solar radiation also has other adverse effects: it causes the skin to lose its elasticity and causes the formation of wrinkles and thus results in premature ageing. Dermatosis is sometimes also observed, and in the extreme case skin cancer can arise.

Owing to this knowledge, changes have also occurred in sun protection. Whereas the main aim a few years ago was erythema-preventing UV-B protection, protection against UV-A radiation is now included in sun-protection preparations.

UV-A radiation is essentially the trigger for pigmentation of the skin.

It is also desirable to protect hair against photochemical damage in order to prevent changes in colour shade, bleaching or damage of a mechanical nature.

As is known, the most dangerous part of solar radiation is formed by ultraviolet rays having a wavelength of less than 400 m. It is also known that the presence of the ozone layer in the earth's atmosphere, which absorbs part of solar radiation, means that the lower limit for the ultraviolet rays which reach the earth's surface is about 280 m. All this knowledge therefore makes the development of efficient filter substances for the UV-A and also for the UV-B region appear necessary.

There is a growing demand for light-protection agents for cosmetic and pharmaceutical preparations which can serve, in particular, as UV-A filters and whose absorption maxima should therefore be in the range from about 320 to 400 m. There is furthermore also a demand for broad-band protection, i.e. UV-A and UV-B protection, in the range 280–400 m.

In order to achieve the desired effect using the smallest possible amount, light-protection agents of this type should additionally have highly specific absorbance. In addition, light-protection agents for cosmetic preparations have to meet a multiplicity of further demands, for example good solubility in cosmetic oils or in water, high stability of the emulsions prepared therewith, toxicological acceptability and low inherent odour and low inherent colour.

A further requirement that light-protection agents have to satisfy is adequate photostability. However, this is often only guaranteed to an inadequate extent with the UV-A and UV-B absorbing light-protection agents available hitherto.

Although the prior art contains various approaches for improving the photostability of good light-protection filters, such as, for example, of dibenzoylmethanes, by combination with various UV-B filters (FR 2 440 933), or also for stabilising the UV filters by addition of certain substances (EP 0514491), adequate solutions are still, however, not available therewith.

Furthermore, DE-A 197 46 656 and EP 0 852 137 propose substance classes, such as 4,4-diarylbutadienes or compounds containing an $R^4$—NH—$CR^3$=$CR^1R^2$ structure, as novel light-protection filters, but these do not adequately meet the demand for suitable compounds for the UV-A and UV-B regions.

The object was therefore to find a novel structural class as light-protection agents for cosmetic and pharmaceutical purposes which absorb in the UV-A and/or UV-B region, are photostable, have low inherent colour, i.e. a sharp band structure, have high absorbance and are soluble in oil or water, depending on the substituent.

It has been found in the earlier application DE 10013318.5 that quinoxaline derivatives containing a wide variety of radicals have excellent UV-B and/or UV-A properties and meet the above-described requirements to a high extent.

It has now been found that specific derivatives of the formula I are particularly suitable for achieving this object.

A first subject-matter of the present invention is therefore the use of compounds of the formula I, reproduced as formulae Ia and Ib,

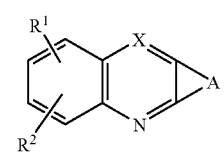

Ia

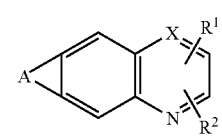

Ib in which
X is an N atom or a C—$R^3$ group
A is a group selected from the formula II or III

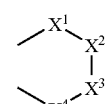

II

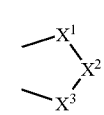

III where
$X^1$, $X^2$, $X^3$ and $X^4$ are each, independently of one another, =N—, —$NR^4$—, —$CR^5R^6$—, —C(=O)— or a =CR— group, with the proviso that, in the formula II, from one to 3 of the $X^1$–$X^4$ groups are selected from =N— and —$NR^4$— and that, in the formula III, one or two of the $X^1$–$X^3$ groups are selected from =N— and —$NR^4$—,
R, $R^1$, $R^2$ and $R^3$ are each, independently of one another, H, alkyl, alkoxy, alkenyl or alkynyl, each having up to 20 carbon atoms, cycloalkyl, cycloalkoxy, cycloalkenyl or bicyclic systems, each having up to 10 carbon atoms, where, in all of these groups, one or more hydrogen atoms may also be substituted by $Sub^1$ and/or one or two $CH_2$ groups may be replaced by C=O, and the cyclic systems may contain from 1 to 3 heteroatoms, such as S, N and/or O, Hal, OH, $NO_2$, —$(CR^5R^6)_n$—$NR^5R^6$, —$(CR^5R^6)_n$—N=$CR^5R^6$, —$(CR^5R^6)_n$—$CR^5$=$NR^5$, —$(CR^5R^6)_n$—$NHCOR^5$, —$(CR^5R^6)_n$—$NHCOOR^5$, —$SR^5$, —$SO_2$—$R^5$, $NR^5$—SO—$R^6$, —SO—$R^5$, water-solubilising substituents selected from the group consisting of carboxylate, sulfonate or ammonium radicals, $COR^5$, $COOR^5$, $CON^5R^6$, CN, O=S(—$R^5$)=O, O=S(—$OR^5$)=O, O=S(—$NR^5R^6$)=O, $R^5OP$(—$OR^6$)=O, OAr, —(CR5R6)n-Ar, —Si(alkyl)3, —Si(alkyl)2H, -Het, —NHHet, —OHet or —(CR5R6)n-Het, $R^1$ and $R^2$ together, also with carbon atoms to which they are bonded, may jointly form an unsaturated, partially or fully saturated 4-, 5-, 6- or 7-membered ring, which may optionally contain heteroatoms, such as S, N and/or O, may be further fused and/or may also be monosubstituted or polysubstituted, $Sub^1$ is Hal, hydroxyl, cyano, amino, nitro, $C_1$–$C_4$-alkylamino, $C_1$–$C_4$-dialkyl-amino, $C_1$–$C_4$-alkyl or $C_1$–$C_4$-alkoxy, COOH or COO-alkyl, Hal is fluorine, chlorine, bromine or iodine, n is 0, 1, 2, 3 or 4, $R^5$ and $R^6$ are each, independently of one another, H, alkyl, alkenyl, alkynyl, each having up to 20 carbon atoms, cycloalkyl, cycloalkenyl, bicyclic systems, each having up to 10 carbon atoms, where these radicals may be up to trisubstituted by $Sub^1$ and/or one or two $CH_2$ groups may be replaced by C=O, and the cyclic systems may also contain from 1 to 3 heteroatoms, such as S, N and/or O, —$(CR'R")_n$—Ar or —$(CR'R")_n$-Het, the radicals $R^5$ and $R^6$ may also, with one another, in each case together with carbon atoms to which they are bonded, jointly form an unsaturated, partially or fully saturated 4-, 5-, 6- or 7-membered ring, which may optionally contain heteroatoms, such as S, N and/or O, may also be monosubstituted or polysubstituted and/or may be further fused, R' and R" are each, independently of one another, H or $C_1$–$C_4$-alkyl, in which one or two $CH_2$ groups may also be replaced by C=O, Ar is an unsubstituted or monosubstituted or polysubstituted aromatic ring or fused ring systems having from 6 to 18 carbon atoms, in which one or two CH groups may also be replaced by C=O, Het is an unsubstituted or monosubstituted or polysubstituted heteroaromatic ring having from 5 to 7 ring members or a fused ring system, where the heteroatoms present are one or more N, S and/or O atoms, and in which one or two CH groups in the α- or β-position to the heteroatoms may also be replaced by C=O, $R^4$ is H, alkyl, alkoxy, alkenyl, alkynyl, each having up to 20 carbon atoms, cycloalkyl, cycloalkoxy, cycloalkenyl, bicyclic systems, each having up to 10 carbon atoms, where these radicals may be up to trisubstituted by $Sub^2$ and/or one or two $CH_2$ groups may be replaced by C=O, and where the cyclic systems may also contain from 1 to 3 heteroatoms, such as S, N and/or O, $Sub^2$ is Hal, hydroxyl, cyano, amino, nitro, $C_1$–$C_4$-alkyl or $C_1$–$C_4$-alkoxy, $COR^5$, $COOR^5$, OAr, OHet, —$(CR^5R^6)_n$—Ar or —$(CR^5R^6)_n$-Het, —$(CR^5R^6)_n$—$NR^5R^6$, $CONR^5R^6$, CN, O=S(—$R^5$)=O, O=S(—$OR^5$)=O, O=S(—$NR^5R^6$)=O or $R^5OP$(—$OR^6$)=O, as photostable UV filters.

The compounds of the formula I according to the invention are also referred to below as quinoxaline derivatives, although compounds which, in the strict chemical sense, are not quinoxaline derivatives are also covered thereby.

The compounds of the formula I can be prepared substantially analogously to the literature. Preparation processes are described, for example, in D. Ames, M. Brohi; J. Chem. Soc perkin. Trans. I (1980) 1384–1389. For a detailed disclosure of the preparation of compounds of the formula I according to the invention, reference is also made, in particular, to the example part of this application (Examples A–G).

The compounds of the formula I exhibit excellent UV-absorbent properties both in the UV-A region and, in the presence of an additional chromophoric group, in the UV-B region, thus providing broad-band protection. The solubility of the substances in water or in cosmetic oils can likewise easily be induced through the choice of suitable substituents. Lipophilic radical, i.e. radicals which increase the oil solubility of the compounds of the formula I are, for example, aliphatic or cycloaliphatic radicals, in particular alkyl radicals having up to 20 carbon atoms, alkoxy, mono- and dialkylamino, alkoxycarbonyl, mono- and dialkylaminocarbonyl, mono- and dialkylaminosulfonyl radicals, furthermore also cyano, nitro, bromine, chlorine, iodine or fluorine substituents.

Hydrophilic radicals, i.e. radicals which facilitate the water solubility of the compounds of the formula I are, for example, carboxyl and sulfoxy radicals and in particular salts thereof with any desired physiologically tolerated cations, such as the alkali metal salts or the trialkylammonium salts.

The alkyl radicals in the radicals R and $R^1$ to $R^6$ have up to 20 carbon atoms and may be in unbranched or branched form and accordingly are preferably methyl, ethyl, n-propyl, i-propyl, butyl, sec-butyl, i-butyl, tert-butyl, pentyl, 1-methylbutyl, 2-methylbutyl, 3-methylbutyl, hexyl, 1-methylpentyl, 2-methylpentyl, heptyl, octyl, nonyl, decyl, undecyl or dodecyl, furthermore also 2,2-dimethylpropyl, 1-ethylpropyl, 3-methylpentyl, 4-methylpentyl, 1,1-dimethylpropyl, 1,2-dimethylpropyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1-ethylhexyl, 2-ethylhexyl, tridecyl, tetradecyl, pentadecyl, hexadecyl, heptadecyl, octadecyl, nonadecyl or eicosyl.

Preferred alkenyl radicals which may be mentioned are branched and unbranched alkenyl chains, preferably having up to 10 carbon atoms: vinyl, propenyl, isopropenyl, 1-butenyl, 2-butenyl, 1-pentenyl, 2-pentenyl, 2-methyl-1-butenyl, 2-methyl-2-butenyl, 3-methyl-1-butenyl, 1-hexenyl, 2-hexenyl, 1-heptenyl, 2-heptenyl, octenyl, nonenyl or decenyl.

Suitable alkynyl radicals are preferably branched or unbranched alkynyl chains having up to 10 carbon atoms, such as, for example, ethynyl, propynyl, butynyl, i-butynyl, pentynyl, hexynyl, heptynyl or octynyl.

Cycloalkyl radicals which may be mentioned are preferably branched or unbranched $C_3$–$C_{10}$-cycloalkyl chains, such as cyclopropyl, cyclobutyl, cyclopentyl, cyclohexyl, cycloheptyl, cyclooctyl, 1-methylcyclopropyl, 1,2-dimethyl-cyclopentyl, 1-methyl-2-ethylcyclopropyl, cyclononyl or cyclodecyl.

Suitable alkoxy radicals are branched or unbranched alkoxy chains having up to 20 carbon atoms, preferably having up to 12 carbon atoms, particularly preferably having from 1 to 8 carbon atoms, such as, for example, methoxy, ethoxy, propoxy, i-propoxy, butoxy, 1-methylpropoxy, 2-methylpropoxy, pentoxy, 1,1-dimethylpropoxy, 1-methylbutoxy, 3-methylbutoxy, 2-methylbutoxy, hexoxy, heptoxy or octoxy.

Cycloalkyl radicals which may be mentioned for R and $R^1$ to $R^6$ are preferably branched or unbranched cycloalkyl chains having 3–10 carbon atoms, such as cyclopropyl, cyclobutyl, cyclopentyl, cyclohexyl, cycloheptyl, 1-methylcyclopropyl, 1-ethylcyclopropyl, 1-propylcyclopropyl, 1,2-dimethylcyclopropyl, 1-methylcyclohexyl, 1,3-dimethylcyclohexyl, cyclooctyl, cyclononyl or cyclodecyl.

Cycloalkenyl radicals which may be mentioned are preferably branched or unbranched $C_3$–$C_{10}$-cycloalkenyl chains having one or more double bonds, such as cyclopropenyl, cyclobutenyl, cyclopentenyl, cyclopentadienyl, cyclohexenyl, 1,3-cyclohexadienyl, 1,4-cyclohexadienyl, cycloheptenyl, cycloheptatrienyl, cyclooctenyl, cyclononenyl or cyclodecenyl.

Bicycloalkyl or bicycloalkenyl radicals which may be mentioned are saturated or unsaturated bicyclic ring systems, preferably having up to 10 carbon atoms, preferably bicyclic terpenes, such as pinane, pinene, bornane or camphor derivatives, decalin or adamantane.

These cyclic systems may also contain from 1 to 3 heteroatoms, such as sulfur, nitrogen or oxygen. Examples thereof which may be mentioned are ring systems, such as piperidine, pyrrolidine, pyrazine or pyridazine, pyrimidine, morpholine, tetrahydrofuran, dihydrofuran, thiolane, piperazine, thiazolidine or oxazolidine groups.

In the radicals above and below which may be substituted by $Sub^1$, $Sub^1$ is preferably halogen, such as fluorine, chlorine, bromine or iodine, preferably fluorine or chlorine, furthermore preferably $C_1$–$C_4$-alkylamino or $C_1$–$C_4$-dialkylamino, $C_1$–$C_4$-alkyl or $C_1$–$C_4$-alkoxy, or alternatively hydroxyl or amino.

In the radicals above and below which may be substituted by $Sub^2$, $Sub^2$ is preferably halogen, such as fluorine, chlorine, bromine or iodine, preferably fluorine or chlorine, furthermore preferably $C_1$–$C_4$-alkylamino or $C_1$–$C_4$-dialkylamino, $C_1$–$C_4$-alkyl or $C_1$–$C_4$-alkoxy, or alternatively hydroxyl or amino, further preference also being given to the meaning $COR^5$, —$(CR^5R^6)_n$—Ar, —$(CR^5R^6)_n$-Het, OAr, OHet, $COOR^5$ or $R^5OP(—OR^6)$=O.

Suitable mono- or dialkylamino radicals are preferably methylamino, dimethylamino, ethylamino, methylethylamino, diethylamino, propylamino, methylpropylamino, dipropylamino, ethylpropylamino, butylamino, dibutylamino, methylbutylamino or isopropylamino, furthermore also 1,1-dimethylpropylamino, pentylamino, hexylamino, 1-methyl-1-ethylpropylamino, heptylamino or octylamino.

In the compounds and formulae above and below, Ar is an unsubstituted or monosubstituted or polysubstituted aromatic ring or a fused ring system having from 6 to 18 carbon atoms, preferably having from 6 to 10 carbon atoms, in which, in addition, one or two CH groups may be replaced by C=O. Particularly preferred groups which may be mentioned are unsubstituted or substituted phenyl or naphthyl.

Het in the definitions above and below is an unsubstituted or monosubstituted or polysubstituted heteroaromatic ring having from 5 to 7 ring members or a fused ring system, preferably having up to 14 ring atoms, in which one or more N, S and/or O atoms are present as heteroatoms and in which, in addition, one or two CH groups may be replaced by C=O. Unless defined otherwise, the heterocyclic rings preferably have 1–13 carbon atoms and 1–6 heteroatoms, in particular 3–9 carbon atoms and 1–4 heteroatoms. For example, heteroaromatic radicals such as 2- or 3-thienyl, 2- or 3-furyl, 2-, 3- or 4-pyridyl, pyrimidyl, pyrazolyl, pyrazolonyl, imidazolyl, triazinyl, pyrazinyl, thiazolyl, indolyl, quinolyl, quinoxalinyl or isoquinolyl are suitable.

The Ar and Het groups described above are preferably unsubstituted or monosubstituted, disubstituted or trisubstituted, possible substituents in principle being all substituents so long as they do not have a toxic effect on the compounds as a whole. The substituents defined as $Sub^2$ are preferably suitable and accordingly preference is given to the following substituents: halogen, in particular F or Cl, hydroxyl, amino, cyano, $C_1$–$C_4$-alkyl or $C_1$–$C_4$-alkoxy, $COR^5$, $COOR^5$, OAr, OHet, —$(CR^5R^6)_n$—Ar or —$(CR^5R^6)_n$-Het, —$(CR^5R^6)_n$—$NR^5R^6$, $CONR^5R^6$, CN, O=S(—$R^5$)=O, O=S(—$OR^5$)=O, O=S(—$NR^5R^6$)=O or $R^5OP(—OR^6)$=O.

It is furthermore also possible for a CH group in the ring system to be replaced by C=N—, i.e. the substituent is then =N—R*, in which R* is the same as $R^5$ or is —NH—Ar.

The following substituents are furthermore very particularly preferred: fluorine, chlorine, —COOH, alkoxy having up to 8 carbon atoms, —COO-alkyl having up to 8 carbon atoms, —CO-phenyl, —CO-aryl, —CO-Het, -quinoxalinyl or —CO—NH—$R^5$. This list has a purely illustrative character and is in no way intended to be limiting.

In the above definitions, the groups Ar, Het, $R^5$ and/or $R^6$ may likewise in turn carry substituents as described above or below for these groups.

The quinoxaline derivative is particularly preferably selected from one of the formulae IV, V, VI and VII

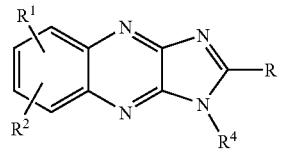

IV

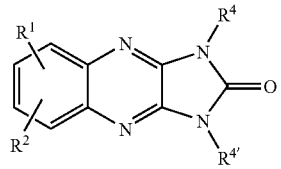

V

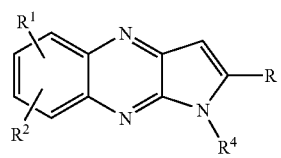

VI

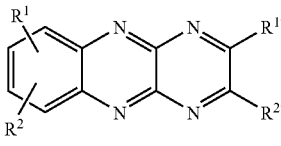

VII in which R, $R^1$, $R^2$ and $R^4$ are as defined above, $R1'$ and $R^{2'}$, independently of one another and of $R^1$ or $R^2$, are likewise as defined above for $R^1$, and $R^{4'}$, independently of $R^4$, is likewise as defined above for $R^4$, where $R^1$, $R^2$, $R^{1'}$, $R^{2'}$, $R^{4'}$ and $R^4$ are preferably H, and R is preferably H, methyl, $^t$butyl or a phenyl ring, which may be monosubstituted or polysubstituted by groups which are as defined above for $R^1$.

Use is preferably made of a quinoxaline derivative selected from the compounds of the formula VIII

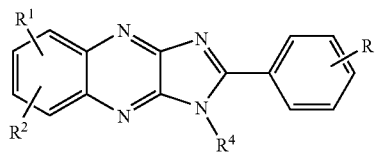

where

R, R1 and R2 are as defined above,

R4 is H or a branched or unbranched C1–20-alkyl radical, in which, if desired, one or more H atoms may be replaced by Sub, Sub and R4 are preferably H, methyl, ethyl or ethyl or ethylhexyl, and R is preferably a branched or unbranched C1–20-alkyl radical, in which, if desired, one or more H atoms may be replaced by Sub. Particular preference is given to compounds in which R is methyl, ethyl, isopropyl or tertiary-butyl. Preference is furthermore given to 1-(2-ethyl-hexyl)-2-phenyl-imidazo[3,4-b]quinoxaline.

It is particularly preferred for the phenyl ring to be substituted in accordance with one of the patterns shown in Table 1.

TABLE 1

| R | m | Position |
|---|---|---|
| $CH_3$ | 1-3 | o/m/p; m/m/p; o/p; m/m |
| $C_2H_5$ | 1-3 | " |
| $C_3H_7$ | 1-3 | " |
| $^nC_4H_9$ | 1-3 | " |
| $^tC_4H_9$ | 1-3 | " |
| $^iC_4H_9$ | 1-3 | " |
| $C_5H_{11}$ | 1-3 | " |
| $C_{18}H_{37}$ | 1-3 | " |
| (2'-Etyl)-hexyl- | 1-3 | " |
| $OCH_3$ | 1-3 | o/m/p; m/m/p; o/p; m/m |
| $OC_2H_5$ | 1-3 | " |
| $OC_3H_7$ | 1-3 | " |
| $OC_4H_9$ | 1-3 | " |
| $OC_5H_{11}$ | 1-3 | " |
| $OC_{18}H_{37}$ | 1-3 | " |
| $OCOCH_3$ | 1-2 | o; m; p; o/p |
| $OCOC_2H_5$ | 1-2 | " |
| $OCOC_3H_7$ | 1-2 | " |
| $OCOC_4H_9$ | 1-2 | " |
| $OCOC_5H_{11}$ | 1-2 | " |
| $OCOC_{18}H_{37}$ | 1-2 | " |
| OH | 1-3 | o/m/p; m/m/p; o/p; m/m |
| F | 1-2 | o; p; o/p |
| Cl | 1-2 | o; p; o/p |
| $CF_3$ | 1 | o; m; p |
| $NO_2$ | 1-3 | m/; m/m; o/o/p |
| $NHCOR^5$ | 1 | p |
| $NHCOOR^5$ | 1 | p |
| $COR^5$ | 1-2 | o; p; o/p |
| $COOR^5$ | 1-2 | o; p; o/p |
| $CONR^5R^6$ | 1-2 | o; p; o/p |
| CN | 1 | p |
| $O=S(OR^5)=O$ | 1 | p |
| $O=S(R^5)=O$ | 1 | p |
| $O=S(NR^5R^6)=O$ | 1 | p |
| $R^5OP(-OR^6)=O$ | 1 | p |

The quinoxaline derivatives according to the invention are outstandingly suitable as UV filter substances. As already mentioned, the quinoxalines can be designed synthetically in such a way that the presence of an additional chromophoric group gives rise to UV-absorbent properties both in the UV-A and in the UV-B region. Broad-band protection can thus be achieved. Furthermore, the solubility of the substances in water or cosmetic oils can be influenced through the choice of substituents.

Some UV-A and UV-B filter substances with which the quinoxalines according to the invention can preferably be combined chemically are listed below (Table 2). This selection is in no way intended to be limiting. The combination can take place through conventional chemical reactions.

TABLE 2

| Combined UV filter | Example |
|---|---|
| 4-Aminobenzoic acid | see formula VIII |
| Dimethoxyphenylglyoxalic acid | |
| 2,2',4,4'-Tetrahydroxybenzophenone | |
| 3,3,5-Trimethylcyclohexyl salicylate | see formula IX |
| 2,2'-Dihydroxy-4-methoxybenzophenone | |
| 5-Methyl-2-(1-methylethyl)2-aminobenzoate | |
| 3-Imidazol-4-ylacrylic acid and ethyl ester | |
| 4-Isopropylbenzyl salicylate | |
| 1-(4'-Isopropylphenyl)-3-phenylpropane-1,3-dione | |
| 3-Benzylidenebornan-2-one (3-benzylidenecamphor) | |
| 3-(4'-Methyl)benzylidenebornan-2-one | see formula X |
| 3-(4'-Trimethylammonium)benzylidenebornan-2-one methylsulfate | |
| 1-(4'-tert-Butylphenyl)-3-(4-methoxyphenyl)propane-1,3-dione (e.g. Eusolex ® 9020) | see formula XI |
| 3-(4' Sulfo)benzylidenebornan-2-one and salts | |
| 2-Hydroxy-4-methoxybenzophenone-5-sulfonic acid/Na salt | |
| 2-Ethylhexyl salicylate | |
| 2-Hydroxy-4-methoxy-4'-methylbenzophenone | |
| 2-Hydroxy-4-methoxybenzophenone | |
| 2-Isoamyl 4-methoxycinnamate | |
| 2-Ethylhexyl 4-methoxycinnamate | |
| 1-Glyceryl 4-aminobenzoate | |

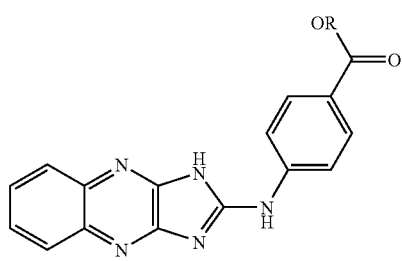

Formula VIII

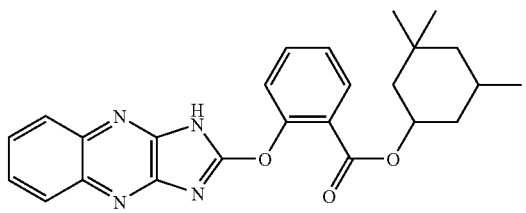

Formula IX

-continued

Formula X

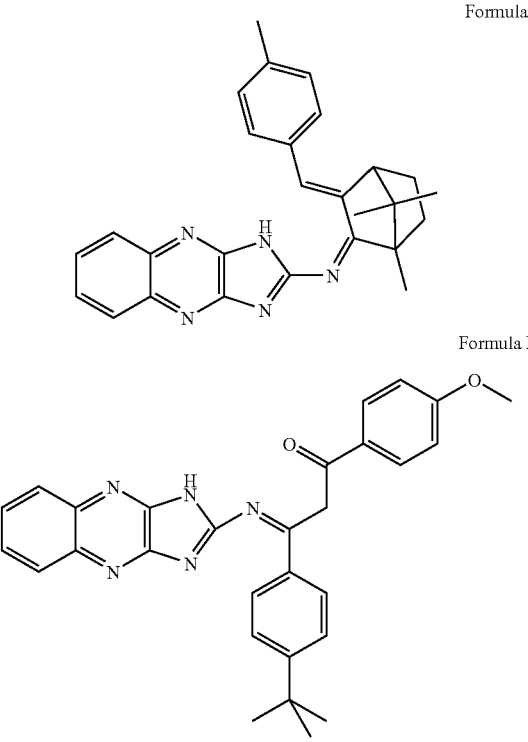

Formula XI

It is therefore particularly preferred in accordance with the invention for at least one of the radicals selected from R and $R^1$ to $R^6$ to correspond to a UV filter from Table 2 bonded via a suitable functional group (preferably an ester, ether, amine, imine, imide or amide function).

The invention also relates to the novel compounds of the formula IV

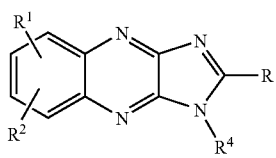

IV in which $R^1$, $R^2$ and $R^4$ are as defined in claim 1, and R is '-butyl or a phenyl ring, which may be monosubstituted or polysubstituted by groups which are as defined for $R^1$ in claim 1, or one of the radicals selected from R and $R^1$, $R^2$ and $R^4$ corresponds to a UV filter from Table 2 bonded via a suitable functional group, preferably an ester, ether, amine, imine, imide or amide function, which are also particularly preferably used.

Particular preference is given here to quinoxaline derivatives of the formula VIII

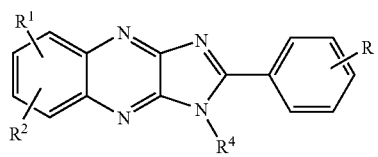

VIII where

R, R1 and R2 are as defined above,

R4 is H or a branched or unbranched C1–20-alkyl radical, in which, if desired, one or more H atoms may be replaced by Sub, Sub is as defined above, and R4 is preferably H, methyl, ethyl or ethyl or ethylhexyl, and R is preferably a branched or unbranched C1–20-alkyl radical, in which, if desired, one or more H atoms may be replaced by Sub. Particular preference is given to compounds of the formula III in which R is methyl, ethyl, isopropyl or tertiary-butyl. Particular preference is furthermore given to 1-(2-ethylhexyl)-2-phenylimidazo[3,4-b]quinoxaline.

The quinoxaline derivatives of the formula IV according to the invention can be prepared starting from 2,3-dichloroquinoxalines which are substituted by $R^1$ and $R^2$ corresponding to the target compound. A process of this type is therefore a further subject-matter of the present invention.

In a preferred variant, a chlorine atom in the 2,3-dichloroquinoxaline is replaced, in a first reaction step, by an amino function. In a further reaction step, the second chlorine atom is preferably replaced by —NH—$R^4$.

In another, likewise preferred process variant, a chlorine atom in the 2,3-dichloroquinoxaline is replaced by —NH—$R^4$ in a first reaction step, and the second chlorine atom is replaced by an amino function in a second reaction step.

Ring closure to give the imidazoquinoxaline according to the invention is then preferably carried out in both cases by reaction with a suitably substituted benzaldehyde derivative.

The choice of suitable reaction conditions for these reactions presents the person skilled in the art with no difficulties at all. Suitable conditions are indicated in Example H for an illustrative example (preparation of 1-(2-ethylhexyl)-2-phenylimidazo[3,4-b]quinoxaline).

If desired, the quinoxaline derivatives can also be combined with any desired UV filter substances, which results in an improvement in the protective performance (SPF boost) through synergistic effects. Some UV-A and UV-B filter substances with which the quinoxalines according to the invention can preferably be combined are listed below. This selection is in no way intended to be limiting. The combination can, besides by direct chemical reaction (as shown above in Table 2), of course also take place through physical combination with UV filters. In principle, all UV filters are suitable for a combination. Particular preference is given to UV filters whose physiological acceptability has already been demonstrated. Substances are known from the specialist literature both for UV-A and UV-B filters, for example benzylidenecamphor derivatives, such as
3-(4'-methylbenzylidene)-dl-camphor (for example Eusolex® 6300),
3-benzylidenecamphor (for example Mexoryl® SD),
polymers of N-{(2 and 4)-[(2-oxoborn-3-ylidene)methyl]benzyl}acrylamide (for example Mexoryl® SW),
N,N,N-trimethyl-4-(2-oxoborn-3-ylidenemethyl)anilinium methylsulfate (for example Mexoryl® SK) or
α-(2-oxoborn-3-ylidene)toluene-4-sulfonic acid (for example Mexoryl® SL), benzoyl- or dibenzoylmethanes, such as
1-(4-tert-butylphenyl)-3-(4-methoxyphenyl)propane-1,3-dione (for example Eusolex® 9020) or
4-isopropyldibenzoylmethane (for example Eusolex® 8020), benzophenones, such as
2-hydroxy-4-methoxybenzophenone (for example Eusolex® 4360) or
2-hydroxy-4-methoxybenzophenone-5-sulfonic acid and its sodium salt (for example Uvinul® MS-40),
methoxycinnamic acid esters, such as
octyl methoxycinnamate (for example Eusolex® 2292),
isopentyl 4-methoxycinnamate, for example as a mixture of the isomers (for example Neo Heliopan® E 1000),
salicylate derivatives, such as
2-ethylhexyl salicylate (for example Eusolex® OS),
4-isopropylbenzyl salicylate (for example Megasol®) or
3,3,5-trimethylcyclohexyl salicylate (for example Eusolex® HMS),
4-aminobenzoic acid and derivatives, such as
4-aminobenzoic acid,
2-ethylhexyl 4-(dimethylamino)benzoate (for example Eusolex® 6007),
ethoxylated ethyl 4-aminobenzoate (for example Uvinul® P25),
and further substances, such as
2-ethylhexyl 2-cyano-3,3-diphenylacrylate (for example Eusolex® OCR),
2-phenylbenzimidazole-5-sulfonic acid and its potassium, sodium and triethanolamine salts (for example Eusolex® 232),
3,3'-(1,4-phenylenedimethylene)bis(7,7-dimethyl-2-oxobicyclo[2.2.1]hept-1-ylmethanesulfonic acid and its salts (for example Mexoryl® SX) and
2,4,6-trianilino-(p-carbo-2'-ethylhexyl-1'-oxy)-1,3,5-triazine (for example Uvinul® T 150).

The compounds mentioned in the list should only be regarded as examples. It is of course also possible to use other UV filters.

These organic UV filters are generally incorporated into cosmetic preparations in an amount of from 0.5 to 10 per cent by weight, preferably 1–8%.

Further suitable organic UV filters are, for example,
2-(2H-benzotriazol-2-yl)-4-methyl-6-(2-methyl-3-(1,3,3,3-tetramethyl-1-(trimethylsilyloxy)disiloxanyl)propyl)phenol (for example Silatrizole®),
2-ethylhexyl 4,4'-[(6-[4-((1,1-dimethylethyl)aminocarbonyl)phenylamino]-1,3,5-triazine-2,4-diyl)diimino]bis(benzoate)(for example UV-Asorb® HEB),
α-(trimethylsilyl)-ω-[trimethylsilyl)oxy]poly[oxy(dimethyl [and approximately 6% of methyl[2-[p-[2,2-bis(ethoxycarbonyl]vinyl]phenoxy]-1-methyleneethyl] and approximately 1.5% of methyl[3-[p-[2,2-bis(ethoxy-carbonyl)vinyl]phenoxy)propenyl) and from 0.1 to 0.4% of (methylhydrogen]silylene]] (n≈60) (CAS No. 207 574-74-1)
2,2'-methylenebis(6-(2H-benzotriazol-2-yl)-4-(1,1,3,3-tetramethylbutyl)-phenol) (CAS No. 103 597-45-1)
2,2'-(1,4-phenylene)bis)-1H-benzimidazole-4,6-disulfonic acid, monosodium salt) (CAS No. 180 898-37-7) and
2,2'-(1,4-phenylene)bis)-1H-benzimidazole-5,5'-monosulfonic acid, monosodium salt
2,4-bis{[4-(2-ethylhexyloxy)-2-hydroxy]phenyl}-6-(4-methoxyphenyl)-1,3,5-triazine (CAS No. 103 597-45-, 187 393-00-6).

These organic UV filters are generally incorporated into cosmetic preparations in an amount of from 0.5 to 20 per cent by weight, preferably 1–15%. They are usually present in formulations according to the invention in weight ratios of from 15:1 to 1:15, preferably from 10:1 to 1:10 and particularly preferably from 5:1 to 1:5 to the quinoxaline derivatives of the formula I.

Preferred compounds having UV-filtering properties are 3-(4'-methylbenzylidene)dl-camphor, 1-(4-tert-butylphenyl)-3-(4-methoxyphenyl)propane-1,3-dione, 4-isopropyldibenzoylmethane, 2-hydroxy-4-methoxybenzophenone, octyl methoxycinnamate, octyl methoxycinnamate, 3,3,5-trimethylcyclohexyl salicylate, 2-ethylhexyl 4-(dimethylamino)benzoate, 2-ethylhexyl 2-cyano-3,3-diphenylacrylate, 2-phenylbenzimidazole-5-sulfonic acid and its potassium, sodium and triethanolamine salts.

Conceivable inorganic UV filters are, for example, those from the group consisting of titanium dioxides, such as, for example, coated titanium dioxide (for example Eusolex® T-2000, Eusolex® T-AQUA), zinc oxides (for example Sachtotec®), iron oxides and also cerium oxides. Titanium oxide and zinc oxide are preferably in the form of micronised inorganic pigments. These inorganic UV filters are generally incorporated into cosmetic preparations in an amount of from 0.5 to 20 per cent by weight, preferably 2–10%. They are usually present in formulations according to the invention in weight ratios of from 25:1 to 1:25, preferably from 10:1 to 1:10 and particularly preferably from 5:1 to 1:5 to the quinoxaline derivatives of the formula I.

The use according to the invention of the quinoxaline derivatives has a further, interesting and advantageous aspect. The combination with other UV filters often results in photostabilisation of these UV fillers by the quinoxaline derivative.

It is known that some UV filters which have advantageous light-protection filter properties per se have the great disadvantage of a certain instability to UV radiation.

For example, the dibenzoylmethane derivatives, such as Eusolex 9020 (4-t-butyl-4'-methoxydibenzoylmethanes), are substances which are exposed to photochemical decomposition. The photochemical decomposition of this class of compounds follows a Norrish type I acyl cleavage. The reaction products formed in the process are no longer available as light-protection filter substances. Although some proposed solutions have already been indicated in the prior art, there nevertheless continues to be a demand for simple and effective ways of effectively countering this photolytic decomposition.

The quinoxaline derivatives described here are outstandingly suitable for this purpose, in particular combination with Eusolex 9020 results in considerably improved photostabilisation of the substance.

In preferred embodiments of the invention, both the compounds of the formula I according to the invention and the conventional UV filters mentioned above can be encapsulated in capsules. It is particularly preferred to encapsulate UV filters which are either not stable on storage in the formulation or tend to penetrate the skin on application. The encapsulation here can be carried out by conventional methods known from the literature. Suitable capsule materials are organic and inorganic polymers. It is particularly preferred to include the UV filters, and in particular also the quinoxaline derivatives of the formula I according to the invention, in oxide capsules, preferably silica capsules, which are preferably produced in a sol-gel process, as described in the international application WO 00/09652.

In accordance with the invention, the UV light-protection filters described here can in each case be used alone or naturally also in combination, which is preferred, in sunscreens. They can be combined with UV-B/A chromophores, for example all filters approved and known worldwide, for improving the protective performance (SPF boost) through synergistic effects. They can preferably be employed in combination both with inorganic and with organic UV-A and UV-B filters or mixtures thereof.

Through combination of one or more compounds of the formula I with further UV filters, the protective action against harmful effects of UV radiation can be optimised.

It is furthermore possible and advantageous to combine the preparations according to the invention with antioxidants. A combination of this type then exhibits both a protective action as antioxidant and also against burns due to UV radiation. A protective action against oxidative stress or against the action of free radicals can thus also be achieved.

The invention therefore also relates to the use of a compound of the formula I according to Claim 1 in combination with antioxidants in cosmetic or pharmaceutical preparations.

The present invention therefore also relates to cosmetic and pharmaceutical preparations which comprise one or more of the compounds of the formula I, optionally in combination with further light-protection agents or antioxidants.

The invention also relates to a method for protecting the skin and natural or sensitised hair against solar radiation, in which an effective amount of at least one compound of the formula I in a cosmetic preparation is applied to the skin or the hair. "Sensitised hair" is taken to mean hair which has been subjected, for example, to permanent-wave treatment, a dyeing process or a bleaching process.

The filters according to the invention for protection against UV-A and UV-B radiation can in each case be incorporated into cosmetic preparations in concentrations of from 0.1 to 20% by weight, preferably from 1 to 15% by weight. In this way, it is possible to prepare preparations in which up to 100% of the light-protection filters employed are the UV filters described here. These are substances which are dissolved, dispersed or emulsified in a simple manner in water and oils, depending on the substituents on the skeleton.

The preparations according to the invention may in addition comprise further conventional skin-protecting or skin-care active ingredients. These may in principle be any active ingredients known to the person skilled in the art.

Particularly preferred active ingredients are pyrimidinecarboxylic acids and/or aryl oximes, as well as coumaranone derivatives.

Pyrimidinecarboxylic acids occur in halophilic microorganisms and play a role in osmoregulation of these organisms (E. A. Galinski et al., Eur. J. Biochem., 149 (1985) pages 135–139). Of the pyrimidinecarboxylic acids, particular mention should be made here of ectoin ((S)-1,4,5,6-tetrahydro-2-methyl-4-pyrimidinecarboxylic acid) and hydroxyectoin ((S,S)-1,4,5,6-tetrahydro-5-hydroxy-2-methyl-4-pyrimidinecarboxylic acid and their derivatives. These compounds stabilise enzymes and other biomolecules in aqueous solutions and organic solvents. Furthermore, they stabilise, in particular, enzymes against denaturing conditions, such as salts, extreme pH values, surfactants, urea, guanidinium chloride and other compounds.

Ectoin and ectoin derivatives, such as hydroxyectoin, can advantageously be used in medicaments. In particular, hydroxyectoin can be employed for the preparation of a medicament for the treatment of skin diseases. Other areas of application of hydroxyectoin and other ectoin derivatives are typically in areas in which, for example, trehalose is used as additive. Thus, ectoin derivatives, such as hydroxyectoin, can be used as protectant in dried yeast and bacteria cells. Pharmaceutical products, such as nonglycosylated, pharmaceutical active peptides and proteins, for example t-PA, can also be protected with ectoin or its derivatives.

Of the cosmetic applications, particular mention should be made of the use of ectoin and ectoin derivatives for the care of aged, dry or irritated skin. Thus, European Patent Application EP-A-0 671 161 describes, in particular, that ectoin and hydroxyectoin are employed in cosmetic preparations, such as powders, soaps, surfactant-containing cleansing products, lipsticks, rouge, makeups, care creams and sunscreen preparations.

Preference is given here to the use of a pyrimidinecarboxylic acid of the following formula,

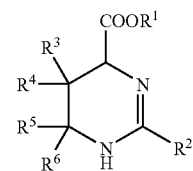

in which $R^1$ is a radical H or C1–8-alkyl, $R^2$ is a radical H or C1–4-alkyl, and $R^3$, $R^4$, $R^5$ and $R^6$ are each, independently of one another, a radical from the group consisting of H, OH, $NH_2$ and C1–4-alkyl. Preference is given to the use of pyrimidinecarboxylic acids in which $R^2$ is a methyl or ethyl group, and $R^1$ or $R^5$ and $R^6$ are H. Particular preference is given to the use of the pyrimidinecarboxylic acids ectoin ((S)-1,4,5,6-tetrahydro-2-methyl-4-pyrimidinecarboxylic acid) and hydroxyectoin ((S,S)-1,4,5,6-tetrahydro-5-hydroxy-2-methyl-4-pyrimidinecarboxylic acid). The preparations according to the invention preferably comprise pyrimidinecarboxylic acids of this type in amounts of up to 15% by weight.

Of the aryl oximes, preference is given to the use of 2-hydroxy-5-methyllaurophenone oxime, which is also known as HMLO, LPO or F5. Its suitability for use in cosmetic compositions is disclosed, for example, in DE-A-41 16 123. Preparations which comprise 2-hydroxy-5-methyllaurophenone oxime are accordingly suitable for the treatment of skin diseases which are accompanied by inflammation. It is known that preparations of this type can be used, for example, for the therapy of psoriasis, various forms of eczema, irritative and toxic dermatitis, UV dermatitis and further allergic and/or inflammatory diseases of the skin and integumentary appendages. Preparations according to the invention which, in addition to the compound of the formula I, additionally comprise an aryl oxime, preferably 2-hydroxy-5-methyllaurophenone oxime, exhibit surprising antiinflammatory suitability. The preparations here preferably comprise from 0.01 to 10% by weight of the aryl oxime, it being particularly preferred for the preparation to comprise from 0.05 to 5% by weight of aryl oxime.

Coumaranone derivatives which may advantageously be present in the preparations according to the invention are compounds of the formula

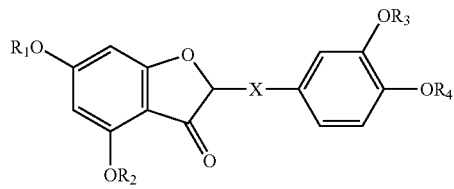

in which —X— is a single bond, —CH$_2$—, =CH—, —C(O)—, =C(OR$^5$)—, —C(NR$^5$)—, —CH(NR$^5$R$^6$)— or —CH(OR$^5$)—, and R$^1$, R$^2$, R$^3$, R$^4$, R$^5$, and R$^6$ may be identical or different and are, independently of one another,

H straight-chain or branched C$_1$- to C$_{12}$-alkyl and/or alkylcarbonyl groups, straight-chain or branched C$_3$- to C$_{12}$-alkenyl and/or -alkenylcarbonyl groups, straight-chain or branched C$_1$- to C$_{12}$-hydroxyalkyl groups, in which the hydroxyl group may be bonded to a primary or secondary carbon atom of the chain, and furthermore the alkyl chain may also be interrupted by oxygen, C$_3$- to C$_{10}$-cycloalkyl and/or cycloalkylcarbonyl groups and C$_3$- to C$_{12}$-cycloalkenyl and/or cycloalkenylcarbonyl groups, in which each of the rings may also be bridged by —(CH$_2$)$_n$— groups, where n= from 1 to 3, aryl and/or arylcarbonyl groups, heteroaryl and/or heteroarylcarbonyl groups, where these groups may be substituted by alkyl, hydroxyl, alkoxy, amino, mono- and dialkylamino, sulfonic acid, carboxyl and/or halogen groups, mono- and/or oligoglycosyl radicals,

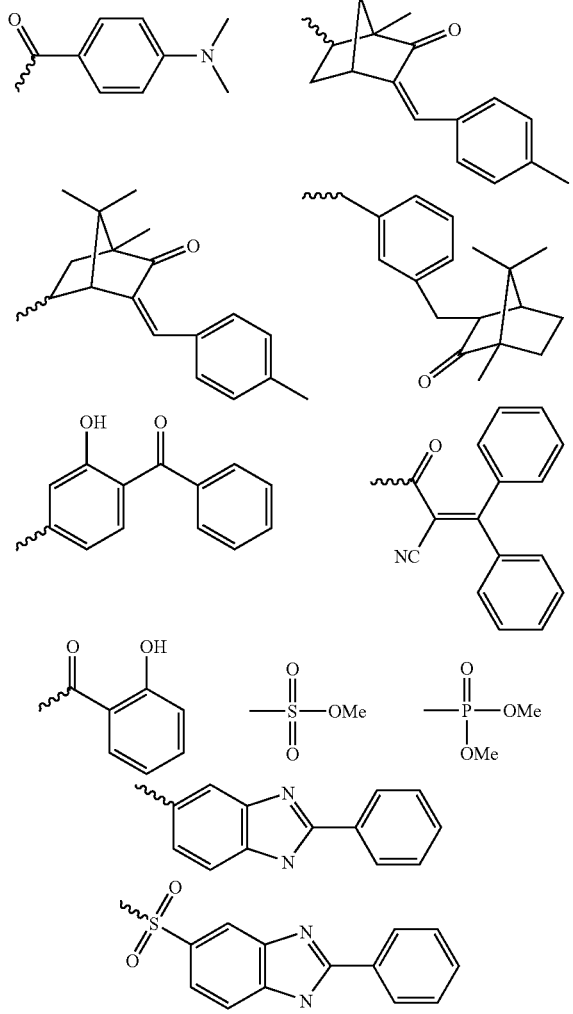

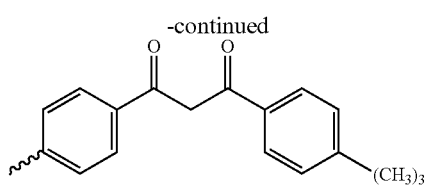

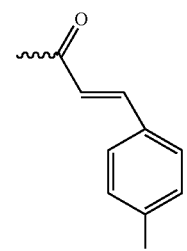

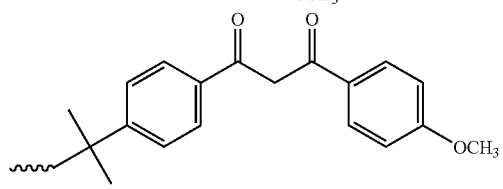

in which Me is a proton or an alkali metal ion, in particular a sodium or potassium ion.

The radicals can thus be bonded to the parent structure as ethers or as esters. Compounds of this type are described in the German patent application DE 10003785.2. Compositions which comprise coumaranone derivatives of this type have a particularly gentle action on the skin, which these compounds exhibit an antioxidant and free-radical-scavenging action.

The parent structure 4,6,3',4'-tetrahydroxybenzyl-3-coumaranone has very good properties. This compound conforms to the above formula, in which X=—CH$_2$—, and R$^1$=R$^2$=R$^3$=R$^4$=H. The solubility of this compound in water can be improved by selecting, for example, the radicals R$^1$, R$^2$, R$^3$ and R$^4$ as sulfate or phosphate groups. A mixture of mono-, di- and trisulfate, which is referred to below as "sulfated coumaranone", is particularly suitable. Particular emphasis should be placed on the trisulfate (X=—CH$_2$—; R$^1$=R$^3$=R$^4$=SO$_3$Me, R$^2$=H), which is represented by the following formula.

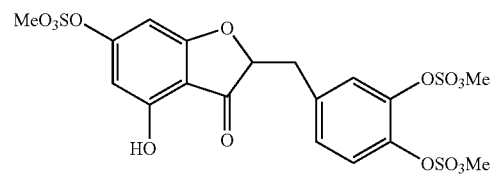

All compounds or components which can be used in the preparations are either known and commercially available or can be synthesised by known processes.

The cosmetic and pharmaceutical preparations comprising light-protection agents are generally based on a vehicle which comprises at least one oil phase. However, preparations on a purely aqueous basis are also possible in the case of the use of compounds having hydrophilic substituents. Accordingly, oils, oil-in-water and water-in-oil emulsions, creams and pastes, lip protection compositions or fat-free gels are possible.

Sunscreen preparations of this type can thus be in liquid, pasty or solid form, for example as water-in-oil creams, oil-in-water creams and lotions, W/O/W systems or O/W/O systems, aerosol foam creams, gels, oils, fat sticks, powders, sprays or alcoholic/aqueous lotions. They can furthermore also be formulated as micronised systems or as PIT (phase inversion temperature) emulsions.

Conventional oil components in cosmetics are, for example, paraffin oil, glyceryl stearate, isopropyl myristate, diisopropyl adipate, acetylstearyl 2-ethyl-hexanoate, hydrogenated polyisobutene, Vaseline, caprylic acid/capric acid triglycerides, microcrystalline wax, lanolin, mineral oils, mineral waxes, esters of fatty acids with alcohols having a low carbon number, for example with isopropanol, propylene glycol or glycerol, alkyl benzoates, silicone oils, such as dimethylpolysiloxanes, diethylpolysiloxanes, diphenylpolysiloxanes, and stearic acid.

The preparations may comprise cosmetic adjuvants which are usually used in preparations of this type, such as, for example, thickeners, softeners, moisturisers, surface-active agents, emulsifiers, preservatives, antifoams, perfumes, fats and waxes, lanolin, propellants, stabilisers, antioxidants, bactericides, dyes and/or pigments which colour the composition itself or the skin, and other ingredients usually used in cosmetics.

Suitable emulsifiers are preferably known W/O and in addition also O/W emulsifiers, such as, for example, polyglycerol esters, sorbitan esters or partially esterified glycerides. Typical examples of fats are glycerides; waxes which should be mentioned are, inter alia, beeswax, carnauba wax, paraffin wax or microwaxes, optionally in combination with hydrophilic waxes. Stabilisers which can be employed are metal salts of fatty acids, such as, for example: magnesium stearate, aluminium stearate and/or zinc stearate. Suitable thickeners are, for example, crosslinked polyacrylic acids and derivatives thereof, polysaccharides, in particular xanthan gum, guar-guar, agar-agar, alginates and tyloses, carboxymethylcellulose and hydroxyethylcellulose, furthermore fatty alcohols, monoglycerides and fatty acids, polyacrylates, polyvinyl alcohol and polyvinylpyrrolidone. It is furthermore also possible to add plant extracts, protein hydrolysates and vitamin complexes.

Antioxidants which can be used are, for example, amino acids, imidazoles, peptides, carotenoids, α-hydroxyacids, unsaturated fatty acids, vitamin A, C and/or E, and suitable derivatives of these substances.

There are many proven substances known from the specialist literature which can be used as antioxidants, for example amino acids (for example glycine, histidine, tyrosine, tryptophan) and derivatives thereof, imidazoles (for example urocanic acid) and derivatives thereof, peptides, such as D,L-carnosine, D-carnosine, L-carnosine and derivatives thereof (for example anserine), carotenoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof), and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (for example buthionine sulfoximines, homocysteine sulfoximine, buthionine sulfones, penta-, hexa- and heptathionine sulfoximine) in very low tolerated doses (for example pmol to μmol/kg), and also (metal) chelating agents, (for example α-hydroxy fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof, vitamin C and derivatives (for example ascorbyl palmitate, magnesium ascorbyl phosphate, ascorbyl acetate), tocopherols and derivatives (for example vitamin E acetate), vitamin A and derivatives (for. example vitamin A palmitate), and coniferyl benzoate of benzoin resin, rutinic acid and derivatives thereof, α-glycosyl rutin, ferulic acid, furfurylideneglucitol, carnosine, butylhydroxytoluene, butylhydroxyanisole, nordohydroguaiaretic acid, trihydroxybutyrophenone, quercetin, uric acid and derivatives thereof, mannose and derivatives thereof, zinc and derivatives thereof (for example ZnO, ZnSO4), selenium and derivatives thereof (for example selenomethionine), stilbenes and derivatives thereof (for example stilbene oxide, transstilbene oxide).

Mixtures of antioxidants are likewise suitable for use in the cosmetic preparations according to the invention. Known and commercial mixtures are, for example, mixtures comprising, as active ingredients, lecithin, L-(+)-ascorbyl palmitate and citric acid (for example Oxynex® AP), natural tocopherols, L-(+)-ascorbyl palmitate, L-(+)-ascorbic acid and citric acid (for example (for example Oxynex® K LIQUID), tocopherol extracts from natural sources, L-(+)-ascorbyl palmitate, L-(+)-ascorbic acid and citric acid (for example Oxynex® L LIQUID), DL-α-tocopherol, L-(+)-ascorbyl palmitate, citric acid and lecithin (for example Oxynex® LM) or butylhydroxytoluene (BHT), L-(+)-ascorbyl palmitate and citric acid (for example Oxynex® 2004).

The quinoxaline derivatives of the formula I are usually present in the formulations according to the invention in weight ratios to the antioxidants of from 10,000:1 to 1:5, preferably from 500:1 to 1:2 and particularly preferably from 50:1 to 1:1.

The preparations according to the invention may comprise vitamins as further ingredients. The cosmetic preparations according to the invention preferably comprise vitamins and vitamin derivatives selected from vitamin A, vitamin A propionate, vitamin A palmitate, vitamin A acetate, retinol, vitamin B, thiamine chloride hydrochloride (vitamin $B_1$), riboflavin (vitamin $B_2$), nicotinamide, vitamin C (ascorbic acid), vitamin D, ergocalciferol (vitamin $D_2$), vitamin E, DL-α-tocopherol, tocopherol E acetate, tocopherol hydrogensuccinate, vitamin $K_1$, esculin (vitamin P active ingredient), thiamine (vitamin $B_1$), nicotinic acid (niacin), pyridoxine, pyridoxal, pyridoxamine, (vitamin $B_6$), panthothenic acid, biotin, folic acid and cobalamine (vitamin $B_{12}$), particularly preferably vitamin A palmitate, vitamin C, DL-α-tocopherol, tocopherol E acetate, nicotinic acid, panthothenic acid and biotin.

The aqueous phase of the preparations according to the invention optionally advantageously comprise alcohols, diols or polyols having a low carbon number, and ethers thereof, preferably ethanol, isopropanol, propylene glycol, glycerol, ethylene glycol, ethylene glycol monoethyl or monobutyl ether, or analogous products, furthermore alcohols such as ethanol, isopropanol, 1,2-propanediol and, in particular, one or more thickeners, such as, for example, silicon dioxide, aluminium silicates, polysaccharides or derivatives thereof, for example hyaluronic acid, xanthan gum or hydroxypropylmethylcellulose, or a polyacrylate from the group consisting of the so-called Carbopols.

Conventional film formers are, for example, hydrocolloids, such as chitosan, microcrystalline chitosan or quaternary chitosan, polyvinylpyrrolidone, vinyl-pyrrolidone-vinyl acetate copolymers, polymers from the acrylic acid series, quaternary cellulose derivatives and similar compounds. Examples of suitable preservatives are formaldehyde solutions, p-hydroxybenzoate or sorbic acid. Suitable pearlescent agents are, for example, glycoldistearic acid esters, such as ethylene glycol distearate, but also fatty acids and fatty acid monoglycol esters. Dyes which can be used are the substances which are suitable and approved for cosmetic purposes, as compiled, for example, in the publication "Kosmetische Färbemittel" [Cosmetic Colorants] by the Dye Commission of the German Research Society, published in Verlag Chemie, Weinheim, 1984. These dyes are usually employed in concentrations of from 0.001 to 0.1% by weight, based on the mixture as a whole.

If desired, the sunscreens according to the invention may also comprise one or more chemical substances having self-tanning properties.

Chemical substances having self-tanning properties which can be employed are all natural and synthetic substances known to the person skilled in the art which are suitable for the preparation of cosmetic preparations. These may be either vegetable extracts or synthetic self-tanning agents, such as, for example, dihydroxyacetone or α-ketols.

If the composition according to the invention is intended to protect natural or sensitised hair against sunlight, it can be in the form of a rinse-out shampoo, lotion, gel or emulsion, the preparation in question being applied before or after shampooing, before or after colouring or bleaching or before or after permanent waving; or the composition is in the form of a lotion or gel for styling and treatment, in the form of a lotion or gel for brushing or blow-waving, in the form of a hair lacquer, hair spray, aerosol foam cream, permanent waving composition, dye or bleach for the hair. In addition to the light-protection filters according to the invention (VIS and/or IR filters) or the combination of light-protection filters according to the invention, this composition may also comprise various adjuvants used in this type of composition, such as surfactants, thickeners, polymers, softeners, preservatives, foam stabilisers, electrolytes, organic solvents, silicone derivatives, oils, waxes, anti-grease agents, dyes and/or pigments which colour the composition itself or the hair, or other ingredients usually used for hair care.

Further typically cosmetic use forms are also lipsticks, lip-care sticks, mascara, eyeliner, eyeshadow, rouge, powder, emulsion and wax make-up, and sun-screen, pre-sun and after-sun preparations.

The light-protection filters according to the invention can be incorporated directly into cosmetic preparations without further preparatory measures.

These substances furthermore offer the great advantage of exhibiting no toxic or allergic reactions with the skin.

The light-protection preparations can advantageously comprise in accordance with the invention, as already described above, further UV filter substances, where the total amount of the filter substances is, for example, from 0.1% by weight to 30% by weight, preferably from 0.5 to 10% by weight, in particular from 1 to 6% by weight, based on the total weight of the preparations.

The preparations according to the invention can furthermore also be used as pharmaceutical compositions for preventative treatment of inflammation and allergies of the skin and also in certain cases for the prevention of certain types of cancer. The pharmaceutical composition according to the invention can be administered orally or topically. For oral administration, the pharmaceutical preparation is in the form of, inter alia, pastilles, gelatine capsules, coated tablets, as a syrup, solution, emulsion or suspension. Topical application is carried out, for example, as an ointment, cream, gel, spray, solution or lotion.

The cosmetic and pharmaceutical preparations according to the invention can be prepared with the aid of methods which are well known to the person skilled in the art.

The properties of compounds of the formula I should likewise be regarded as positive for use in foods, as food supplements, as dietary agent or as functional food. The further explanations given for foods logically also apply to food supplements and functional foods.

The foods which can be enriched in accordance with the present invention with one or more of the compounds according to the invention include all materials which are suitable for consumption by animals or consumption by humans, for example vitamins and provitamins thereof, fats, minerals or amino acids. (The foods may be solid, but also liquid, i.e. in the form of a beverage). Foods which can be enriched with one or more compounds of the formula I in accordance with the present invention are, for example, also foods which originate from a single natural source, such as, for example, sugar, unsweetened juice, squash or puree of a single plant species, such as, for example, unsweetened apple juice (for example also a mixture of different types of apple juice), grapefruit juice, orange juice, apple compote, apricot squash, tomato juice, tomato sauce, tomato puree, etc. Further examples of foods which can be enriched with one or more compounds of the formula I in accordance with the present invention are corn or cereals from a single plant species and materials produced from plant species of this type, such as, for example, cereal syrup, rye flour, wheat flour or oatbran. Mixtures of foods of this type are also suitable for being enriched in accordance with the present invention with one or more of the compounds according to the invention, for example multivitamin preparations, mineral mixtures or sweetened juice. As further examples of foods, mention may be made of food preparations, for example prepared cereals, biscuits, mixed drinks, foods prepared especially for children, such as yoghurt, diet foods, low-calorie foods or animal feeds.

The foods which can be enriched in accordance with the present invention with one or more compounds of the formula I thus include all edible combinations of carbohydrates, lipids, proteins, inorganic elements, trace elements, vitamins, water or active metabolites of plants and animals.

The foods which can be enriched in accordance with the present invention with one or more compounds of the formula I are preferably administered orally, for example in the form of meals, pills, tablets, capsules, powders, syrup, solutions or suspensions.

These enriched foods according to the invention can be prepared using techniques which are well known to the person skilled in the art.

Even without further comments, it is assumed that a person skilled in the art will be able to utilise the above description in its broadest scope. The preferred embodiments should therefore merely be regarded as descriptive disclosure which is absolutely not limiting in any way.

The following examples are intended to illustrate the present invention without limiting it. All amount data, proportions and percentages are, unless stated otherwise, based on the weight and the total amount or the total weight of the preparations.

The complete disclosure content of all applications and publications mentioned above and below are incorporated into this application by way of reference.

PREPARATION EXAMPLES

Example A

Synthesis of 1H-pyrazolo[3,4-b]quinoxalines (A and B)

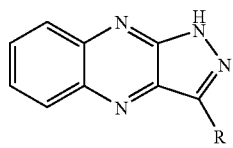

A: R = Me
B: R = Ph

Preparation: 320 mg of 2-carbonyl-3-chloroquinoxaline (1.55 mmol) and hydrazine hydrate (194 mg, 3.88 mmol) are heated at the boil for 72 hours in THF. The solvent is removed by distillation, and water (50 ml) and saturated sodium hydrogencarbonate solution (10 ml) are added to the residue. The mixture is extracted with chloroform (3×100 ml), and the combined organic phases are dried over magnesium sulfate. The solvent is removed by distillation, and recrystallisation of the residue from cyclohexane/tert-butyl methyl ether gives 3-methyl-1H-pyrazoloquinoxaline and 3-phenyl-1H-pyrazoloquinoxaline in a yield of 80% and 97% respectively.

| Characterisation of 3-methyl-1H-pyrazolo[3,4-b]quinoxaline (A) Melting point: 225° C. | |
|---|---|
| 300 MHz $^1$H-NMR (CDCl$_3$): | |
| δ = 13.55 | (s br., 1H, —NH, exchangeable with D$_2$O) |
| 8.19–7.71 | (m, 4H, hetaryl arom.) |
| 2.66 | (s, 3H, CH$_3$) |
| 75 MHz $^{13}$C-NMR (CDCl$_3$): | |
| δ = 143.76 | (quat. C) |
| 142.20 | (quat. C) |
| 140.94 | (quat. C) |
| 139.79 | (quat. C) |
| 135.59 | (quat. C) |
| 130.46 | (tert. C) |
| 129.80 | (tert. C) |
| 128.16 | (tert. C) |
| 128.24 | (tert. C) |
| 11.43 | (—CH$_3$) |
| MS(70 eV): m/e (%) = | 185(13) [M$^+$ + 1], 184(100) [M$^+$], 183(12), 143(40), 116(20), 102(10), 90(10) |
| C$_{10}$H$_8$N$_4$ (184.20 g/mol): | Calc. [%] C 65.21 H 4.38 N 30.42 Found [%] C 64.92 H 4.36 N 30.23 |

| Characterisation of 3-phenyl-1H-pyrazolo[3,4-b]quinoxaline (B) Melting point: 251° C. | |
|---|---|
| 300 MHz $^1$H-NMR (CDCl$_3$): | |
| δ = 14.35 | (s br., 1H, NH, exchangeable with D$_2$O) |
| 8.63–7.35 | (m, 4H, hetaryl, 5H, phenyl) |
| 8.31–8.63 | (m$_c$, 4H, hetaryl arom.) |
| 7.35–7.89 | (m$_c$, 5H, arom.) |
| 75 MHz $^{13}$C-NMR (CDCl$_3$): | |
| δ = 144.27 | (quat. C) |
| 141.61 | (quat. C) |
| 140.88 | (quat. C) |
| 140.50 | (quat. C) |
| 134.62 | (quat. C) |
| 133.64 | (quat. C) |
| 131.00 | (quat. C) |
| 130.11 | (quat. C) |
| 128.83 | (3 × tert. C) |
| 128.40 | (tert. C) |
| 128.01 | (tert. C) |
| 126.24 | (2 × tert. C) |
| MS(70 eV): m/e (%) = | 247(18) [M+ + 1], 246(100) [M+], 245(15), 219(17), 143(18), 116(17), 89(10), 58(10) |
| C$_{15}$H$_{10}$N$_4$ (246.27 g/mol): | Calc. [%] C 73.16 H 4.09 N 22.75 Found [%] C 73.22 H 4.18 N 22.58 |

Example B

Synthesis of N-arylpyrrolo[2,3-b]quinoxalines

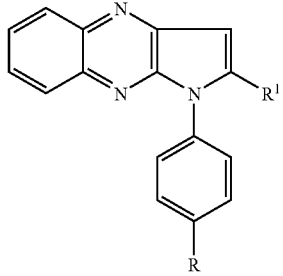

A: R = CO$_2$C(CH$_3$)$_3$, R$^1$ = Ph
B: R = COCH$_3$, R$^1$ = Si(iPr)$_3$
C: R = COOH, R$^1$ = H
D: R = H, R$^1$ = Si(iPr)$_3$
E: R = COCH$_3$, R$^1$ = H

Preparation: 1.05 mmol the aromatic amine are added to a solution of 1.00 mmol of the 2-alkynyl-3-chloroquinoxaline in a polar solvent (anhydrous) (R$^1$=H or Ph; Si(iPr)$_3$: THF), and the mixture is refluxed for 2–12 hours. The solid which precipitates during the reaction or due to evaporation of the solution is filtered off and purified by recrystallisation from ethanol/ethyl acetate or by column chromatography on silica gel using cyclohexane/ethyl acetate (1:1). The pyrroloquinoxalines are obtained in yields of 53–88%.

| Characterisation of N-[4(t-butoxycarbonyl)phenyl]-2-phenyl[2,3-b]pyrroloquinoxaline (A) IR (KBr): | | |
|---|---|---|
| Wavenumber [cm$^{-1}$] = | 3132 | (ν (N—R), NR$_2$) |
| | 3065 | (ν (C—H), Ph) |
| | 2973 | (ν (C—H), t-butyl) |
| | 1710 | (ν (C=O), CO$_2$R) |
| | 1617 | (ν (C=C), Ph) |
| | 1499 | (ν (C=C), Ph) |
| | 1341 | ((skeleton), Ph) |
| | 1308 | ((skeleton), Ph) |
| | 792 | (γ (C—H), Ph) |
| | 762 | (γ (C—H), Ph) |

-continued

300 MHz $^1$H-NMR (CDCl$_3$):

| | | |
|---|---|---|
| δ = | 8.17–8.20 | (m, 1H, hetaryl arom.) |
| | 8.03–8.08 | (m, 1H, hetaryl arom.) |
| | 7.99–8.02 | (m, 2H, arom.) |
| | 7.73–7.78 | (m, 2H, hetaryl arom.) |
| | 7.54–7.57 | (m, 2H, arom.) |
| | 7.43–7.49 | (m, 5H, arom.) |
| | 7.30 | (s, 1H, hetaryl arom.) |
| | 1.58 | (s, 9H, C$_4$H$_9$) |

75 MHz $^{13}$C-NMR (CDCl$_3$):

| | | |
|---|---|---|
| δ = | 166.64 | (C$_{quat}$, CO$_2$R) |
| | 150.89 | (C$_{quat}$, arom.) |
| | 143.71 | (C$_{quat}$, arom.) |
| | 142.65 | (C$_{quat}$, arom.) |
| | 140.80 | (C$_{quat}$, arom.) |
| | 139.59 | (C$_{quat}$, arom.) |
| | 138.50 | (C$_{quat}$, arom.) |
| | 130.11 | (C—H, arom.) |
| | 129.83 | (C—H, arom.) |
| | 129.58 | (C—H, arom.) |
| | 129.01 | (C—H, arom.) |
| | 128.68 | (C—H, arom.) |
| | 128.44 | (C—H, arom.) |
| | 128.07 | (C—H, arom.) |
| | 127.98 | (C—H, arom.) |
| | 127.24 | (C—H, arom.) |
| | 102.06 | (C-3, pyrrole) |
| | 51.43 | (C(CH$_3$)$_3$) |
| | 27.67 | (C(CH$_3$)$_3$) |

MS(70 eV): m/e (%) = 422(16) [M$^+$ + 1], 421(58) [M$^+$], 406(2), 360 (100), 349(9) 321(37), 295(2), 218(1), 191 (2), 174(4), 137(2), 128(3), 120(5), 102 (4), 91(2), 76(4)

Characterisation of N-[4-(acetyl)phenyl]-2-(triisopropyl)silylpyrrolo[2,3-b]-quinoxaline (B)
IR (KBr):

| | | |
|---|---|---|
| Wavenumber [cm$^{-1}$] = | 3183 | (ν (N—R), NR2) |
| | 3046 | (ν (C—H), Ph) |
| | 1697 | (ν (C=O), COCH3) |
| | 1643 | (ν (C=C), Ph) |
| | 1597 | (ν (C=C), Ph) |
| | 1583 | (ν (C=C), Ph) |
| | 1347 | ((skeleton), Ph) |
| | 1282 | ((skeleton), Ph) |
| | 841 | (γ (Si—C), SiR3) |
| | 755 | (γ (C—H), Ph) |

300 MHz $^1$H-NMR (CDCl3):

| | | |
|---|---|---|
| δ = | 8.32 | (m, 1H, hetaryl arom.) |
| | 8.05–8.08 | (m, 1H, hetaryl arom.) |
| | 7.98–8.01 | (m, 2H, arom.) |
| | 7.71–7.77 | (m, 2H, hetaryl arom.) |
| | 7.56–7.59 | (m, 2H, arom.) |
| | 7.25 | (s, 1H, hetaryl arom.) |
| | 2.14 | (s, 3H, CH3) |
| | 1.35 | (sep, 3H, CH) |
| | 1.13 | (s, 9H, CH3) |
| | 1.09 | (d, 9H, CH3) |

MS(70 eV): m/e (%) = 443(3) [M+], 373(2), 344(1), 303(43), 301(100), 286(1), 261(63), 259(25), 245(7), 231(68), 217(7), 195(11), 181(8), 153(7), 122(19), 103(43), 93(13), 79(6)

| | |
|---|---|
| HRMS (high resolution mass) (EI) (C$_{27}$H$_{33}$N$_3$OSi) [M$^+$] | Calc. for: 443, 2447<br>Found for: 443, 2446 |

Characterisation of 4-[N-(pyrrolo[2,3-b]quinoxaline)]benzoic acid (C)
IR (KBr):

| | | |
|---|---|---|
| Wavenumber [cm$^{-1}$] = | 3133 | (ν (N—R), NR2) |
| | 3056 | (ν (C—H), Ph) |
| | 1710 | (γ (C=O)) |
| | 1611 | (γ (C=C), Ph) |
| | 1493 | (γ (C=C), Ph) |
| | 1414 | ((skeleton), Ph) |
| | 1348 | ((skeleton), Ph) |
| | 762 | (γ (C—H), Ph) |

MS(70 eV): m/e (%) = 365 [M$^+$] (100), 364(61), 319(37), 262(7), 217(2), 183(6), 102(9), 90(8), 65(12), 28(7)

300 MHz $^1$H-NMR (DMSO):

| | | |
|---|---|---|
| δ = | 8.17 | (m$_c$, 1H, hetaryl arom.) |
| | 8.05–8.08 | (m$_c$, 2H, arom.) |
| | 7.99 | (m$_c$, 1H, hetaryl arom.) |
| | 7.73–7.77 | (m$_c$, 2H, hetaryl arom.) |
| | 7.56–7.57 | (m$_c$, 1H, arom.) |
| | 7.53 | (m$_c$, 1H, arom.) |
| | 7.42–7.48 | (m$_c$, 1H, arom.) |
| | 7.22 | (s, 1H, hetaryl arom.) |

$^{13}$C-NMR (DMSO):

| | | |
|---|---|---|
| δ = | 166.65 | (C=O) |
| | 150.94 | (C$_{quat}$, arom.) |
| | 142.61 | (C$_{quat}$, arom.) |
| | 140.74 | (C$_{quat}$, arom.) |
| | 139.59 | (C$_{quat}$, arom.) |
| | 138.49 | (C$_{quat}$, arom.) |
| | 131.13 | (C—H, arom.) |
| | 130.12 | (C—H, arom.) |
| | 129.81 | (C—H, arom.) |
| | 129.59 | (C—H, arom.) |
| | 129.01 | (C—H, arom.) |
| | 128.67 | (C—H, arom.) |
| | 128.44 | (C—H, arom.) |
| | 127.99 | (C—H, arom.) |
| | 127.27 | (C—H, arom.) |
| | 102.02 | (C-3, pyrrole) |

Characterisation of 2-(triisopropyl)silylpyrrolo[2,3-b]quinoxaline (D)
IR (KBr):

| | | |
|---|---|---|
| Wavenumber [cm$^{-1}$] = | 3467 cm$^{-1}$ | (ν (NH), NR$_2$) |
| | 3138 | (ν (C—H), hetaryl) |
| | 2967 | (ν (C—H), alkyl) |
| | 1637 | (γ (C=C), hetaryl) |
| | 1558 | (γ (C=C), hetaryl) |
| | 1440 | (γ (C=C), hetaryl) |
| | 1387 | ((skeleton), hetaryl) |
| | 1249 | ((skeleton), hetaryl) |
| | 880 | (γ (Si—C), SiR$_3$) |
| | 762 | (γ (C—H), hetaryl) |

MS(70 eV): m/e (%) = 325 [M$^+$] (42), 282(100), 254(20), 240(18), 226(16), 212(24), 196(5), 181(1), 153(3), 113(11), 84(16), 74(6), 43(7)

300 MHz $^1$H-NMR (CDCl$_3$):

| | | |
|---|---|---|
| δ = | 7.68–7.80 | (m$_c$, 1H, hetaryl arom.) |
| | 7.51–7.56 | (m$_c$, 2H, arom.) |
| | 7.35–7.40 | (m$_c$, 1H, arom.) |
| | 7.09 | (s, 1H, hetaryl arom.) |

Characterisation of N-[4-(acetyl)phenyl]pyrrolo[2,3-b]quinoxaline (E)
IR (KBr):

| | | |
|---|---|---|
| Wavenumber [cm$^{-1}$] = | 3131 | (ν (NH), NR$_2$) |
| | 3052 | (ν (C—H), Ph) |
| | 1690 | (γ (C=O), COCH$_3$) |
| | 1611 | (γ (C=C), Ph) |
| | 1499 | (γ (C=C), Ph) |
| | 1420 | ((skeleton), Ph) |
| | 1348 | ((skeleton), Ph) |
| | 848 | (γ (Si—C), SiR$_3$) |
| | 782 | (ν (C—H), Ph) |

MS(70 eV): m/e (%) = 364 [M$^+$ + 1] (35), 363 [M$^+$] (100), 362 [M$^+$ − 1] (46), 348(9), 320(69), 294(5), 174(5), 127(12), 84(13), 70(48), 43(34)

-continued

300 MHz $^1$H-NMR (CDCl$_3$):

| | | |
|---|---|---|
| δ = | 8.36 | (m$_c$, 1H, hetaryl arom.) |
| | 8.04–8.08 | (m$_c$, 3H, hetaryl arom.) |
| | 7.69–7.70 | (m$_c$, 2H, arom.) |
| | 7.50–7.52 | (m$_c$, 2H, arom.) |
| | 7.38–7.42 | (m$_c$, 5H, arom.) |
| | 6.82 | (s, 1H, hetaryl arom.) |
| | 2.64 | (s, 3H, C$\underline{H}_3$) |

300 MHz $^{13}$C-NMR (CDCl$_3$):

| | | |
|---|---|---|
| δ = | 197.03 | (C$_{quat}$, arom.) |
| | 151.41 | (C$_{quat}$, arom.) |
| | 144.40 | (C$_{quat}$, arom.) |
| | 141.72 | (C$_{quat}$, arom.) |
| | 140.08 | (C$_{quat}$, arom.) |
| | 139.50 | (C$_{quat}$, arom.) |
| | 135.87 | (C$_{quat}$, arom.) |
| | 130.69 | (C—H, arom.) |
| | 129.78 | (C—H, arom.) |
| | 129.22 | (C—H, arom.) |
| | 128.86 | (C—H, arom.) |
| | 128.76 | (C—H, arom.) |
| | 128.05 | (C—H, arom.) |
| | 128.02 | (C—H, arom.) |
| | 127.72 | (C—H, arom.) |
| | 127.36 | (C—H, arom.) |
| | 102.75 | (C-3, pyrrole) |
| | 26.63 | (C$\underline{H}_3$) |

Example C

Synthesis of 1-H-pyrrolo[2,3-b]quinoxaline, 2-phenyl-1H-pyrrolo-[2,3-b]quinoxaline and 2-(triisopropyl)silyl-1-H-pyrrolo[2,3-b]quinoxaline

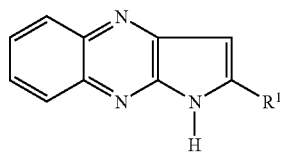

A: R$^1$ = Ph
B: R$^1$ = H
C: R$^1$ = Si(iPr)$_3$

Preparation: KOtBu (potassium tert-butoxide, 1.95 mmol) is added under an inert-gas atmosphere to a solution of (1.5 mmol) of 3-alkynyl-2-aminoquinoxa-line in 1.5 ml of NMP (N-methylpyrrolidone; anhydrous), and the mixture is left to stir at room temperature for 4–6 hours. 1.5 ml of H$_2$O are subsequently added, and the mixture is extracted with dichloromethane (3×10 ml). After washing with NaCl solution and drying over MgSO$_4$, the residue is purified by column chromatography on silica gel using cyclohexane/ethyl acetate (2:1). The 1-H-pyrrolo[2,3-b]quinoxalines can be obtained in yields of 64–97%.

Characterisation of 2-phenyl-1H-pyrrolo[2,3-b]quinoxaline (A)
IR (KBr):

| | | |
|---|---|---|
| Wavenumber [cm$^{-1}$] = | 3107 | (ν (N—H), NH) |
| | 3085 | (ν (C—H), Ph) |
| | 1604 | (ν (C=C), Ph) |
| | 1564 | (ν (C=C), Ph) |
| | 1499 | (ν (C—H), Ph) |
| | 1341 | ((skeleton), Ph) |
| | 848 | (γ (C—H), Ph) |
| | 759 | (γ (C—H), Ph) |

300 MHz $^1$H-NMR (DMSO):

| | | |
|---|---|---|
| δ = | 12.55 | (br.s, 1H, NH) |
| | 8.14–8.17 | (m, 2H, hetaryl arom.) |
| | 8.07–8.10 | (m, 1H, hetaryl arom.) |
| | 8.03–8.05 | (m, 1H, hetaryl arom.) |
| | 7.68–7.72 | (m, 2H, arom.) |
| | 7.53–7.60 | (m, 3H, arom.) |
| | 7.30 | (s, 1H, hetaryl arom.) |

75 MHz $^{13}$C-NMR (DMSO):

| | | |
|---|---|---|
| δ = | 149.30 | (C$_{quat}$, arom.) |
| | 143.65 | (C$_{quat}$, arom.) |
| | 140.32 | (C$_{quat}$, arom.) |
| | 138.78 | (C$_{quat}$, arom.) |
| | 130.13 | (C—H, arom.) |
| | 129.14 | (C—H, arom.) |
| | 128.54 | (C—H, arom.) |
| | 127.83 | (C—H, arom.) |
| | 127.09 | (C—H, arom.) |
| | 126.43 | (C—H, arom.) |
| | 126.32 | (C—H, arom.) |
| | 95.56 | (C-3, pyrrole) |

MS(70 eV): m/e (%) = 246(15) [M$^+$ + 1], 245(100) [M$^+$], 244(6), 142 (11), 128(7), 116(8), 102(24), 90(22), 77(21)

Characterisation of 1-H-pyrrolo[2,3-b]quinoxaline (B)
IR (KBr):

| | | |
|---|---|---|
| Wavenumber [cm$^{-1}$] = | 3105 | (ν (N—H), NH) |
| | 2940 | (ν (C—H), pyrrole) |
| | 1564 | (ν (C=C), hetaryl) |
| | 1535 | (ν (C=C), hetaryl) |
| | 1341 | ((skeleton), hetaryl) |
| | 762 | (γ (C—H), hetaryl) |

300 MHz $^1$H-NMR (CDCl$_3$):

| | | |
|---|---|---|
| δ = | 12.07 | (br.s, 1H, NH) |
| | 8.30–8.31 | (m, 1H, hetaryl arom.) |
| | 8.12–8.15 | (m, 1H, hetaryl arom.) |
| | 8.05–8.09 | (m, 1H, hetaryl arom.) |
| | 7.68–7.75 | (m, 1H, hetaryl arom.) |
| | 7.58–7.64 | (m, 1H, H-2) |
| | 6.74–6.76 | (m, 1H, H-3) |

MS(70 eV): m/e (%) = 169(100) [M$^+$], 168(6), 142(14), 129(1), 118(7), 102(8), 90(5), 76(2)

Characterisation of 2-(triisopropyl)silyl-1-H-pyrrolo[2,3-b]quinoxaline (C)
IR (KBr):

| | | |
|---|---|---|
| Wavenumber [cm$^{-1}$] = | 3302 | (ν (N—H), NH) |
| | 2966 | (ν (C—H), i-R) |
| | 1637 | (ν (C=C), hetaryl) |
| | 1611 | (ν (C=C), hetaryl) |
| | 1558 | (ν (C=C), hetaryl) |
| | 1505 | (ν (C=C), hetaryl) |
| | 1249 | ((skeleton), hetaryl) |
| | 880 | (γ (Si—C), SiR$_3$) |
| | 762 | (γ (C—H), hetaryl) |

300 MHz $^1$H-NMR (CDCl$_3$):

| | | |
|---|---|---|
| δ = | 7.83–7.85 | (m, 1H, hetaryl arom.) |
| | 7.50–7.53 | (m, 2H, hetaryl arom.) |
| | 7.37–7.39 | (m, 1H, hetaryl arom.) |
| | 7.34 | (s, 1H, hetaryl arom.) |
| | 5.51 | (br.s, 1H, NH) |
| | 1.15 | (sep, 3H, CH) |
| | 1.13 | (s, 9H, CH$_3$) |
| | 1.09 | (s, 9H, CH$_3$) |

MS(70 eV): m/e (%) = 325 [M$^+$] (36), 298(9), 282(100), 266(1), 254 (31), 240(8), 226(14), 212(20), 196(5), 170(1), 153(9), 112(14), 98(3), 84(26), 76(8)

Example D

Synthesis of

A: 1,4-dihydropyrazino[2,3-b]quinoxaline-2,3-dione
B: 1-hydropyrazino[2,3-b]quinoxalin-2,3-one

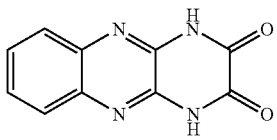
A

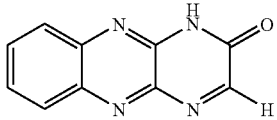
B

Preparation: Glyoxalic acid monohydrate or oxalic acid dihydrate (1.10 mmol) is added to a solution of 2,3-diaminoquinoxaline (1.0 mmol) in ethanol (anhydrous), and the mixture is left to stir at room temperature for 48 hours with addition of a few drops of glacial acetic acid. After evaporation of the solution, a precipitate deposits, which can be purified by washing with cold ethanol (A) or by column chromatography (B) on silica gel using an ethyl acetate/ethanol eluent mixture. The condensed quinoxalines are obtainable in the form of pale-yellow powders in a yield of 68% (A) and 79% (B).

| Characterisation of 1,4-dihydropyrazino[2,3-b]quinoxaline-2,3-(A) IR (KBr): | | |
|---|---|---|
| Wavenumber [cm$^{-1}$] = | 3309 | ($\nu$ (N—H), NH) |
| | 3052 | ($\nu$ (C—H), hetaryl) |
| | 1690 | ($\nu$ (C=O)) |
| | 1624 | ($\nu$ (C=C), hetaryl) |
| | 1506 | ($\nu$ (C=C), hetaryl) |
| | 1249 | ((skeleton), hetaryl) |
| | 755 | ($\gamma$ (C—H), hetaryl) |
| 300 MHz $^1$H-NMR (CDCl$_3$): | | |
| $\delta$ = | 11.96 | (br.s, 2H, NH) |
| | 7.16–7.21 | (m, 2H, hetaryl arom.) |
| | 7.09–7.14 | (m, 2H, hetaryl arom.) |
| 75 MHz $^{13}$C-NMR (CDCl$_3$): | | |
| $\delta$ = | 154.43 | (C$_{quat}$, C=O) |
| | 126.27 | (C$_{quat}$ arom.) |
| | 124.54 | (C$_{quat}$ arom.) |
| | 124.78 | (C—H, arom.) |
| | 123.12 | (C—H, arom.) |
| | 122.17 | (C—H, arom.) |
| | 114.31 | (C—H, arom.) |
| MS(70 eV): m/e (%) = 214(2) [M$^+$], 186(1), 160(100), 144(10), 133(88), 116(4), 106(51), 90(25), 79(26) | | |

| Characterisation of 1-hydropyrazino[2,3-b]quinoxaline-2,3-(B) IR (KBr): | | |
|---|---|---|
| Wavenumber [cm$^{-1}$] = | 3374 | ($\nu$ (N—H), NH) |
| | 3058 | ($\nu$ (C—H), hetaryl) |
| | 1703 | ($\nu$ (C=O)) |
| | 1644 | ($\nu$ (C=N), hetaryl) |
| | 1585 | ($\nu$ (C=C), hetaryl) |
| | 1493 | ((skeleton), hetaryl) |
| | 1341 | ((skeleton), hetaryl) |
| | 1262 | ((skeleton), hetaryl) |
| | 762 | ($\gamma$ (C—H), hetaryl) |
| 300 MHz $^1$H-NMR (CDCl$_3$): | | |
| $\delta$ = | 11.93 | (br.s, 1H, NH) |
| | 9.21 | (s, 1H, H-3) |
| | 7.61–7.73 | (m$_c$, 2H, H-5, H-8) |
| | 7.43–7.56 | (m$_c$, 2H, H-6, H-7) |
| MS(70 eV): m/e (%) = 198(96) [M$^+$], 186(16), 170(76), 158(7), 143(100), 133(5), 116(52), 102(19), 90(34), 76(14), 63(12) | | |

Example E

Synthesis of 2-aryl-1H-imidazo[4,5-b]quinoxalines or 2-aryl-1-methylimidazo[4,5-b]quinoxalines

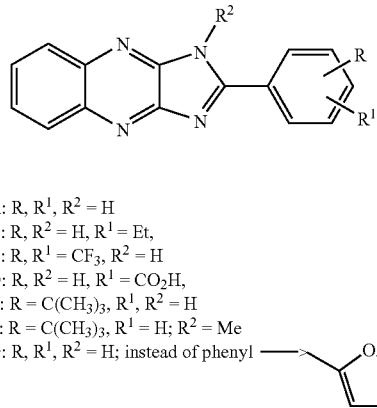

A: R, R$^1$, R$^2$ = H
B: R, R$^2$ = H, R$^1$ = Et,
C: R, R$^1$ = CF$_3$, R$^2$ = H
D: R, R$^2$ = H, R$^1$ = CO$_2$H,
E: R = C(CH$_3$)$_3$, R$^1$, R$^2$ = H
F: R = C(CH$_3$)$_3$, R$^1$ = H; R$^2$ = Me
G: R, R$^1$, R$^2$ = H; instead of phenyl 

Preparation: 0.98 mmol of the aroyl chloride (freshly distilled) is added to a solution of 1.00 mmol of diaminoquinoxaline (160 mg) in 15.0 ml of a polar aprotic solvent (preferably THF or dioxane/dried), and the mixture is refluxed for 48–72 hours. After cooling, the solvent is removed, and the residue is purified by column chromatography on silica gel using a cyclohexane/ethyl acetate→ethyl acetate/ethanol solvent/eluent mixture. The products can be obtained as pale-yellow powders in a yield of 33–76%.

A: 2-phenyl-1H-imidazo[4,5-b]quinoxaline
B: 2-[4-[(ethyl)phenyl]-1H-imidazo[4,5-b]quinoxaline
C: 2-[3,5-bis (trifluoromethyl)phenyl]-1H-imidazo[4,5-b]quinoxaline
D: 2-[4-(carboxy)phenyl]-1H-imidazo[4,5-b]quinoxaline
E: 2-[4-[(t-butyl)phenyl]-1H-imidazo[4,5-b]quinoxaline
F: 2-[4-[(t-butyl)phenyl]-1-methylimidazo[4,5-b]quinoxaline
G: 2-(2-furyl)-1H-imidazo[4,5-b]quinoxaline

| Characterisation of 2-phenyl-1H-imidazo[4,5-b]quinoxaline (A) IR (KBr): | | |
|---|---|---|
| Wavenumber [cm$^{-1}$] = | 3058 | ($\nu$ (C—H), Ph) |
| | 1611 | ($\nu$ (C=C), Ph) |
| | 1538 | ($\nu$ (C=C), Ph) |
| | 1348 | ((skeleton), Ph) |
| | 755 | ($\gamma$ (C—H), Ph) |

-continued

300 MHz $^1$H-NMR (CDCl$_3$):

| δ = | 12.86 | (br.s, 1H, NH) |
|---|---|---|
| | 8.42–8.45 | (m, 2H, hetaryl arom.) |
| | 8.11–8.16 | (m, 2H, hetaryl arom.) |
| | 7.75–7.80 | (m, 2H, arom.) |
| | 7.66–7.72 | (m, 3H, arom.) |

MS(70 eV): m/e (%) = 247(16.2) [M$^+$ + 1], 246(100) [M$^+$], 245(4), 219 (5), 143(52), 116(24), 104(4), 90(6), 77(4)

Characterisation of 2-[4-[(ethyl)phenyl]-1H-imidazo[4,5-b]quinoxaline (B)
IR (KBr):

| Wavenumber [cm$^{-1}$] = | 3039 | (ν (C—H), Ph) |
|---|---|---|
| | 2960 | (ν (C—H), C$_2$H$_5$) |
| | 1617 | (ν (C=C), Ph) |
| | 1545 | (ν (C=C), Ph) |
| | 1492 | (ν (C=C), Ph) |
| | 1335 | ((skeleton), Ph) |
| | 769 | (γ (C—H), Ph) |

300 MHz $^1$H-NMR (CDCl$_3$):

| δ = | 13.84 | (br.s, 1H, NH) |
|---|---|---|
| | 8.32–8.35 | (m, 2H, arom.) |
| | 8.12 | (m, 2H, hetaryl arom.) |
| | 7.74–7.78 | (m, 2H, hetaryl arom.) |
| | 7.52 | (m, 2H, arom.) |
| | 2.74 | (q, 2H, CH$_2$) |
| | 1.25 | (t, 3H, CH$_3$) |

75 MHz $^{13}$C-NMR (CDCl$_3$):

| δ = | 167.23 | (C$_{quat.}$, arom.) |
|---|---|---|
| | 166.27 | (C$_{quat.}$, arom.) |
| | 161.97 | (C$_{quat.}$, arom.) |
| | 155.12 | (C$_{quat.}$, arom.) |
| | 149.03 | (C$_{quat.}$, arom.) |
| | 147.18 | (C$_{quat.}$, arom.) |
| | 131.63 | (C$_{quat.}$, arom.) |
| | 130.15 | (C—H, arom.) |
| | 129.35 | (C—H, arom.) |
| | 128.64 | (C—H, arom.) |
| | 128.15 | (C—H, arom.) |
| | 127.99 | (C—H, arom.) |
| | 127.88 | (C—H, arom.) |
| | 127.73 | (C—H, arom.) |
| | 127.50 | (C—H, arom.) |
| | 28.17 | (CH$_2$CH$_3$) |
| | 15.29 | (CH$_2$CH$_3$) |

MS(70 eV): m/e (%) = 275(19) [M$^+$ + 1], 274(100) [M$^+$], 273(14), 245(3), 259(39), 143(11), 116(14), 102(2), 89(3), 77(1)
(HRMS) (high resolution mass) C$_{17}$H$_{14}$N$_4$ [M$^+$]   Calc. for: 274, 1219
Found for: 274, 1217

Characterisation of 2-[3,5-bis(trifluoromethyl)phenyl]-1H-imidazo[4,5-b]quinox-aline (C)
IR (KBr):

| Wavenumber [cm$^{-1}$] = | 3065 | (ν (C—H), Ph) |
|---|---|---|
| | 1657 | (ν (C=C), Ph) |
| | 1282 | (ν (C=F), Ph) |
| | 1181 | ((skeleton), Ph) |
| | 781 | (γ (C—H), Ph) |

300 MHz $^1$H-NMR (CDCl$_3$):

| δ = | 11.83 | (br. s, 1H, NH) |
|---|---|---|
| | 9.94 | (m, 2H, arom.) |
| | 8.25 | (m, 1H, arom.) |
| | 8.00–8.06 | (m, 2H, hetaryl arom.) |
| | 7.65–7.70 | (m, 2H, hetaryl arom.) |

MS(70 eV): m/e (%) = 383(20) [M$^+$ + 1], 382(100) [M$^+$], 381(3), 363(9), 313(1), 220(2), 170(2), 143(90), 116(39), 102(5), 90(19), 76(2)

Characterisation of 2-[4-(carboxy)phenyl]-1H-imidazo[4,5-b]quinoxaline (D)
IR (KBr):

| Wavenumber [cm$^{-1}$] = | 3472 | (ν (O—H), OH) |
|---|---|---|
| | 3056 | (ν (C—H), Ph) |
| | 1697 | (ν (C=O), CO$_2$H) |
| | 1637 | (ν (C=C), Ph) |
| | 1512 | (ν (C=C), Ph) |
| | 1472 | (ν (C=C), Ph) |
| | 1341 | ((skeleton), Ph) |
| | 1288 | ((skeleton), Ph) |
| | 755 | (γ (C—H), Ph) |

300 MHz $^1$H-NMR (CDCl$_3$):

| δ = | 11.93 | (br. s, 1H, NH) |
|---|---|---|
| | 8.49–8.52 | (m, 1H, arom.) |
| | 8.13–8.14 | (m, 1H, arom.) |
| | 8.10–8.12 | (m, 2H, hetaryl arom.) |
| | 7.71–7.75 | (m, 2H, hetaryl arom.) |
| | 7.30–7.34 | (m, 1H, arom.) |
| | 7.12–7.10 | (m, 1H, arom.) |
| | 6.75 | (br. s, 1H, OH) |

MS(70 eV): m/e (%) = 290 [M$^+$] (5), 169(7), 160(97), 149(16), 133(100), 116(8), 105(13), 91(34), 79(23)

Characterisation of 2-(2-furyl)-1H-imidazo[4,5-b]quinoxaline (G)
IR (KBr):

| Wavenumber [cm$^{-1}$] = | 3111 | (ν (C=H), furyl) |
|---|---|---|
| | 2960 | (ν (C—O—C), furyl) |
| | 1623 | (ν (C=C), hetaryl) |
| | 1525 | (ν (C=C), hetaryl) |
| | 1327 | ((skeleton), hetaryl) |
| | 1268 | ((skeleton), hetaryl) |
| | 775 | (γ (C—H), hetaryl) |

300 MHz $^1$H-NMR (CDCl$_3$):

| δ = | 14.06 | (br. s, 1H, NH) |
|---|---|---|
| | 8.26–8.27 | (m, 1H, furyl arom.) |
| | 8.14–8.19 | (m, 2H, hetaryl arom.) |
| | 7.98–8.04 | (m, 2H, hetaryl arom.) |
| | 7.78–7.74 | (m, 1H, furyl arom.) |
| | 6.96–6.98 | (m, 1H, furyl arom.) |

MS(70 eV): m/e (%) = 238(13) [M$^+$ + 1], 237(100 [M$^+$], 236(3), 208(2), 161(25), 143(62), 133(11), 116(32), 105(9), 95(12), 90(7), 77(5)

Characterisation of 2-[4-[(t-butyl)phenyl]-1-methylimidazo[4,5-b]quinoxaline (F)

(HRMS) (high resolution mass) (E1) C$_{20}$H$_{20}$N$_4$ [M$^+$] Calc. for: 316.1697
Found for: 316.1701
IR (KBr):

| Wavenumber [cm$^{-1}$] = | 3065 | (ν (C—H), Ph) |
|---|---|---|
| | 2960 | (ν (C—H), alkyl) |
| | 1617 | (γ (C=C), Ph) |
| | 1545 | (γ (C=C), Ph) |
| | 1485 | (γ (C=C), Ph) |
| | 1446 | (γ (C=C), Ph) |
| | 1382 | ((skeleton), Ph) |
| | 1341 | ((skeleton), Ph) |
| | 1123 | ((skeleton), Ph) |
| | 867 | (γ (C—H), Ph) |
| | 755 | (γ (C—H), Ph) |

MS(70 eV): m/e (%) = 317 [M$^+$ + 1], 316 [M$^+$] (65), 301(100), 273(7), 258(5), 150(12), 128(21), 103(9), 90(6), 77(3), 57(1)

300 MHz $^1$H-NMR (CDCl$_3$):

| δ = | 8.17–8.20 | (m$_c$, 1H, H-8', hetaryl arom.) |
|---|---|---|
| | 8.03–8.07 | (m$_c$, 1H, H-7', hetaryl arom.) |
| | 7.88–7.91 | (m$_c$, 2H, H-2, H-6, arom.) |

-continued

| | | |
|---|---|---|
| | 7.61–7.64 | (m_c, 1H, H-6', H-9' hetaryl arom.) |
| | 7.52–7.55 | (m_c, 2H, H-3, H-5, arom. |
| | 4.09 | (s, 3H, C$\underline{H}_3$) |
| | 1.30 | (s, 9H, C(C$\underline{H}_3$)$_3$) |
| $^{13}$C-NMR (CDCl$_3$): | | |
| δ = | 163.49 | (C-2') |
| | 155.44 | (C-4) |
| | 150.17 | (C-5') |
| | 143.43 | (C-4') |
| | 141.79 | (C-10') |
| | 139.95 | (C-9') |
| | 129.68 | (C—H) |
| | 128.13 | (C—H) |
| | 128.05 | (C—H) |
| | 127.43 | (C—H) |
| | 126.13 | (C-3) |
| | 125.72 | (C-5) |
| | 35.24 | ($\underline{C}$(CH$_3$)$_3$) |
| | 31.24 | (C($\underline{C}$H$_3$)$_3$) |
| | 29.85 | ($\underline{C}$H$_3$) |

Example F

Synthesis of 2-aryl-4-methylimidazo[4,5-b]quinoxalines

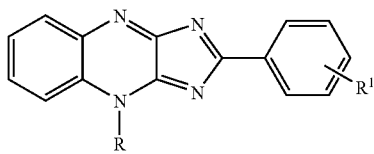

A: R=Me; R$^1$=C(CH$_3$)$_3$

Characterisation of 2-[4-[(t-butyl)phenyl]-4-methylimidazo[4,5-b]quinoxaline (A)

| Characterisation of 2-[4-[(t-butyl)phenyl]-4-methylimidazo[4,5-b]quinoxaline (A) IR (KBr): | | |
|---|---|---|
| Wavenumber [cm$^{-1}$] = | 3058 | (ν (C—H), Ph) |
| | 2954 | (ν (C—H), alkyl) |
| | 2861 | (ν (C—H), alkyl) |
| | 1604 | (γ (C=C), Ph) |
| | 1486 | (γ (C=C), Ph) |
| | 1454 | (γ (C=C), Ph) |
| | 1354 | ((skeleton), Ph) |
| | 1259 | ((skeleton), Ph) |
| | 769 | (γ (C—H), Ph) |
| MS(70 eV): m/e (%) = | 317 [M$^+$ + 1] (32), 302(100), 273(3), 158(1), 131(2) | |
| 300 MHz $^1$H-NMR (CDCl$_3$): | | |
| δ = | 8.51–8.54 | (m_c, 2H, H-2, H-6, arom.) |
| | 8.23–8.26 | (m_c, 1H, H-8', hetaryl arom.) |
| | 7.74–7.78 | (m_c, 1H, H-7', hetaryl arom.) |
| | 7.67–7.70 | (m_c, 1H, H-6', hetaryl arom.) |
| | 7.59–7.65 | (m_c, 1H, H-9', hetaryl arom.) |
| | 7.48–7.51 | (m_c, 2H, H-3, H-5, arom.) |
| | 4.43 | (s, 3H, C$\underline{H}_3$) |
| | 1.28 | (s, 9H, C(C$\underline{H}_3$)$_3$) |

-continued

| Characterisation of 2-[4-[(t-butyl)phenyl]-4-methylimidazo[4,5-b]quinoxaline (A) IR (KBr): | | |
|---|---|---|
| $^{13}$C-NMR (CDCl$_3$): | | |
| δ = | 163.51 | (C-2') |
| | 156.35 | (C-4) |
| | 138.21 | (C-5') |
| | 131.26 | (C-4') |
| | 130.50 | (C—H) |
| | 129.79 | (C—H) |
| | 128.92 | (C—H) |
| | 125.83 | (C—H) |
| | 114.73 | (C-5') |
| | 35.24 | ((C$\underline{H}_3$)$_3$) |
| | 34.28 | (C$\underline{H}_3$) |
| | 31.26 | ($\underline{C}$(CH$_3$)$_3$) |

Example G

Synthesis of 2-tert-butyl-1H-imidazoquinoxaline

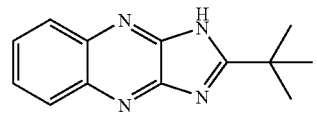

Preparation: 0.98 mmol of the pivaloyl anhydride (206 mg) is added to a solution of 1.00 mmol of diaminoquinoxaline (160 mg) in 15.0 ml of a polar aprotic solvent (preferably THF or dioxane/dried), and the mixture is refluxed for 48–72 hours. After cooling, the solvent is removed in a rotary evaporator, and the residue is purified by column chromatography on silica gel using a cyclohexane/ethyl acetate→ethyl acetate/ethanol solvent/eluent mixture. The 2-tert-butyl-1H-imidazoquinoxaline can be obtained as a beige-white powder.

| IR (KBr): | 3355 | (ν(N—H), NH) |
|---|---|---|
| Wavenumber [cm$^{-1}$] | 3085 | (ν(C—H), Ph) |
| | 2980 | (ν(C—H), CH$_3$) |
| | 1623 | (ν(C=N), hetaryl) |
| | 1611 | (ν(C=C), Ph) |
| | 1518 | (ν(C=C), Ph) |
| | 1334 | ((skeleton), Ph) |
| | 768 | (γ(C—H), aryl) |
| $^1$H-NMR (300 MHz, d-CDCl$_3$): | 11.13 | (br · s, 1H, NH) |
| | 8.16–8.18 | (m, 2H, hetaryl, arom.) |
| δ = | 7.71–7.74 | (m, 2H, hetaryl, arom.) |
| | 1.60 | (s, 9H, CH$_3$) |
| $^{13}$C (75.4 MHz) | 158.27; 140.44; | (C$_{quat}$, hetaryl, arom.) |
| δ = | 128.40; 125.18 | |
| | 128.80; 127.89 | (C—H, hetaryl, arom.) |
| | 34.92 | (C$_{quat}$, $\underline{C}$(CH$_3$)$_3$)) |
| | 28.88 | (C(C$\underline{H}_3$)) |
| MS: m/e (%) = | 226 (32) [M$^+$], 211 (100), 184 (17), 161 (5), 144 (14), 133 (3), 116 (14), 102 (3), 90 (10), 71 (18) | |

Example H

Preparation of 1-(2-ethylhexyl)-2-phenylimidazo[3,4-b]quinoxaline a) Route A: Preparation of 2-amino-3-chloroquinoxaline

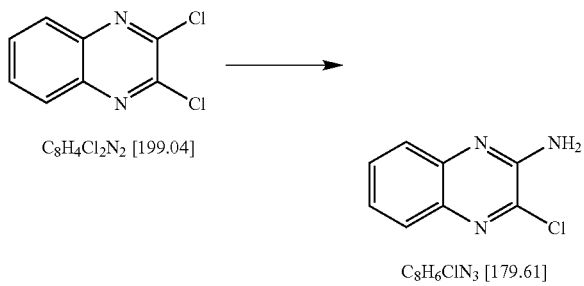

2.1 g (10.4 mmol) of 2,3-dichloroquinoxaline are stirred for 8 hours with 50 ml of 20% ethanolic ammonia in an autoclave at 80°–85° C. and autogenous pressure. The reaction solution is evaporated to dryness in a rotary evaporator, and the crude product is chromatographed over silica gel using toluene/ethyl acetate. The product-containing fractions are collected and evaporated in a rotary evaporator. Yield: 1.18 g (63%)

b) Route B: Preparation of 2-chloro-3-(2-ethylhexylamino)quinoxaline

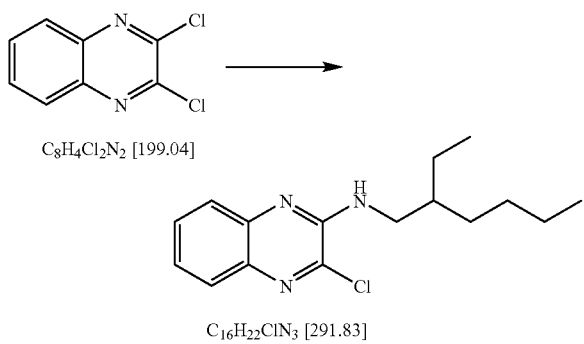

12 g (60.3 mmol) of 2,3-dichloroquinoxaline are dissolved in 125 ml of THF with 9.5 g (72.1 mmol) of diisopropylethylamine. 8.5 g (66 mmol) of 2-ethylhexylamine are added dropwise to the solution, and the reaction is refluxed for a total of 48 hours until starting material is no longer visible according to TLC (silica gel: n-heptane/MTB ether). The reaction solution is evaporated to dryness in a rotary evaporator, and the crude product is chromatographed over silica gel using n-heptane/MTB ether. The product-containing fractions are collected and evaporated in a rotary evaporator. Yield: 11.8 g (67%)

c) Route A: Preparation of 2-amino-3-(2-ethylhexylamino)quinoxaline from 2-amino-3-chloroquinoxaline

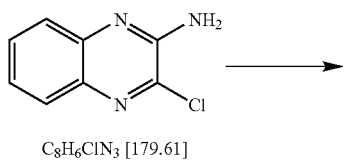

-continued

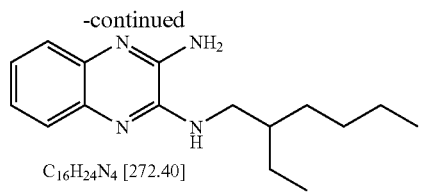

1.8 g (10 mmol) of 2-amino-3-chloroquinoxaline are dissolved in 85 ml of THF with 2.5 g (19 mmol) of diisopropylethylamine. 1.6 g (12 mmol) of 2-ethylhexylamine are added dropwise to the solution, and the reaction is refluxed for a total of 48 hours until starting material is no longer visible according to TLC (silica gel: n-heptane/MTB ether). The reaction solution is evaporated to dryness in a rotary evaporator, and the crude product is chromatographed over silica gel using toluene/ethyl acetate. The product-containing fractions are collected and evaporated in a rotary evaporator. Yield: 1.9 g (71%)

d) Route B: Preparation of 2-amino-3-(2-ethylhexylamino)quinoxaline from 2-chloro-3-(2-ethylhexylamino)quinoxaline

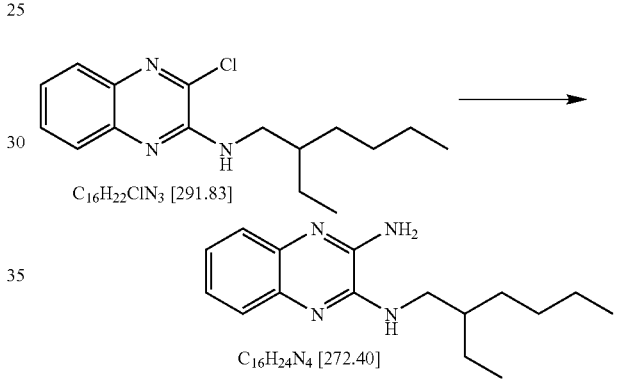

11.5 g of 2-chloro-3-(2-ethylhexylamino)quinoxaline are stirred for 48 hours with 200 ml of 20% ethanolic ammonia at 90°–100° C. and autogenous pressure. After the autoclave has been cooled, the methanol is distilled off, and the crude product is separated off from the starting material (10%) by chromatography over silica gel using toluene/ethyl acetate. Yield: 7.9 g (73%)

e) Preparation of 1-(2-ethylhexyl)-2-phenylimidazo[3,4-b]quinoxaline

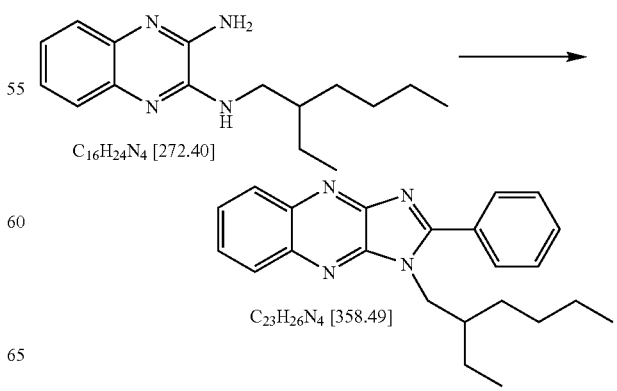

1.38 g (5.1 mmol) of 2-amino-3-(2-ethylhexylamino) quinoxaline are dissolved in 20 ml of DMF, and 0.94 g (5 mmol) of sodium disulfite is added to the solution. 0.57 g (5.3 mmol) of benzaldehyde is added to the suspension, and the reaction is heated at 110° C. for 8 hours until the conversion is complete. After the reaction solution has been cooled to room temperature, 50 ml of MTB ether and 50 ml of water are added, the phases are separated, the aqueous phase is subsequently extracted with 30 ml of MTB ether, and the organic phases are evaporated to dryness (1.73 g; 96% yield) in a rotary evaporator. For further purification, the crude product is recrystallised from n-heptane. Yield: 0.98 g (54%)

The spectra (MS and $^1$H-NMR) available for the individual reactions a)–e) in each case correspond to expectations.

Example J

The following table shows the structural formulae of quinoxaline derivatives which can be employed in accordance with the invention and the maxima of their UV-A and UV-B absorption. The measurement was carried out in 2-propanol at a concentration of 1 mg of substance per 100 ml of solvent.

| Structural formula | UV-A (400 320 nm) | | UV-B (280 320 nm) | |
|---|---|---|---|---|
| | Max. abs. | λ[nm] | Max. abs. | λ[nm] |
| 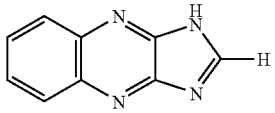 | 0.5227 | 328.0 | | |
| 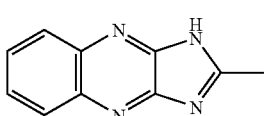 | 0.5824 | 327.5 | | |
| 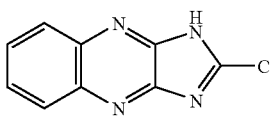 | 0.4875 | 327.5 | | |
| 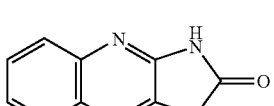 | 0.3754<br>0.3381<br>0.3707 | 342.0<br>335.0<br>327.5 | | |
| 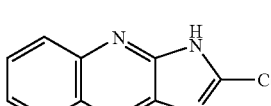 | 0.6290 | 330.0 | | |
| 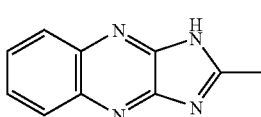 | 0.9293<br>0.9565 | 368.0<br>354.0 | | |
| 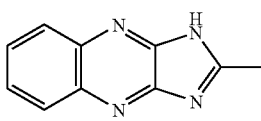 | 1.478<br>1.4581<br>0.7467<br>0.7403 | 372.0<br>358.0<br>372.0<br>358.0 | | |
| 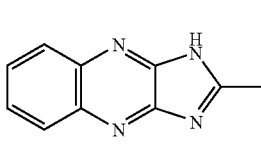 | 0.7037 | 358.0 | | |

-continued

| Structural formula | UV-A (400 320 nm) | | UV-B (280 320 nm) | |
|---|---|---|---|---|
| | Max. abs. | λ[nm] | Max. abs. | λ[nm] |
| [pyrrolo-quinoxaline with N-(4-acetylphenyl) and 2-phenyl substituents] | 0.4067 | 359.0 | | |
| [pyrrolo-quinoxaline with R³ = phenyl-CO₂t-Bu and 2-phenyl]; :R³ = (phenyl)CO₂t-Bu | 0.4496 | 358.0 | 0.5643 | 269.0 |
| [pyrrolo-quinoxaline with NH and 2-phenyl] | 0.7158 | 367.0 | 0.8710 | 268.0 |
| [pyrazino-quinoxaline with R², R³ = OH] | 0.6909 | 327.0 | | |
| [pyrrolo-quinoxaline, NH] | 0.5381 | 338.0 | | |
| [pyrrolo-quinoxaline with N-(4-acetylphenyl) and 2-Si(-)₃] | 0.5774 | 403.0 | 0.4246 | 318.0 |

-continued

| Structural formula | UV-A (400 320 nm) | | UV-B (280 320 nm) | |
|---|---|---|---|---|
| | Max. abs. | λ[nm] | Max. abs. | λ[nm] |
| (structure shown) | 0.3685 | 358.0 | | |

Use Examples

Example 1

Preparation of a sunscreen spray (O/W) according to the invention

| | | % |
|---|---|---|
| A | | |
| 2-tert-Butyl-1H-imidazoquinoxaline | (1) | 1.00 |
| Eusolex 2292 (Art. No. 105382) | (1) | 7.50 |
| (Octyl Methoxycinnamate) | | |
| Eusolex HMS (Art. No. 111412) | (1) | 7.00 |
| (Homosalate) | | |
| Volpo S-2 (Steareth-2) | (2) | 0.40 |
| Volpo S-10 (Steareth-10) | (2) | 0.80 |
| Pemulen TR-2 | (3) | 0.18 |
| (Acrylate/C10-39Alkyl Acrylate Crosspolymer) | | |
| Hetester PHA | (4) | 5.00 |
| (Propylene Glycol Isoceteth-3 Acetate) | | |
| Performa V 825 | (5) | 0.80 |
| (Synthetic Wax) | | |
| Dow Corning 200 (100 cs) | (6) | 1.00 |
| (Dimethicone) | | |
| Oxynex K Liquid (Art. No. 108324) | (1) | 0.10 |
| (PEG-8 (and) Tocopherol (and) Ascorbyl Palmitate (and) Ascorbic Acid (and) Citric Acid) | | |
| B | | |
| Eusolex 232 (Art. No. 105372) | (1) | 1.00 |
| (Phenylbenzimidazole Sulfonic Acid) | | |
| Triethanolamine (Art. No. 108379) | (1) | 0.90 |
| Propane-1,2-diol (Art. No. 107478) | (1) | 2.00 |
| Preservatives | | q.s. |
| Water, Demineralised | | to 100.00 |

Preparation:

For neutralisation of Eusolex 232, the triethanolamine is introduced into the water of phase B, and Eusolex 232 is added with stirring. After complete dissolution, the remaining raw materials of phase B are added and heated to 80° C. Add phase A apart from the Pemulen and heat to 80° C. Stir Pemulen into phase A. Add phase B slowly to phase A with stirring, homogenise and cool with stirring.

Notes:

The preservatives used are:
0.05% of propyl 4-hydroxybenzoate (Art. No. 107427)
0.15% of methyl 4-hydroxybenzoate (Art. No. 106757)

Sources of Supply:
(1) Merck KGaA, Darmstadt
(2) Croda, Nettetal
(3) Goodrich, Neuss
(4) ROVI, Schlüchtern
(5) New Phase, N.J. 08554
(6) Dow Corning, Wiesbaden

Example 2

Preparation of a sunscreen gel (O/W) according to the invention

| | | % |
|---|---|---|
| A | | |
| 2-tert-Butyl-1H-imidazoquinoxaline | (1) | 1.00 |
| Eusolex 6300 (Art. No. 5385) | (1) | 10.00 |
| Luvitol EHO | (2) | 2.00 |
| Dow Corning 200 (100 cs) | (3) | 2.00 |
| Shea Butter | (4) | 5.00 |
| Antaron V-220 | (5) | 2.00 |
| Oxynex K Liquid (Art. No. 8324) | (6) | 1.00 |
| B | | |
| Eusolex 232 (Art. No. 5372) | (1) | 0.75 |
| Tris(hydroxymethyl)aminomethane (Art. No. 8386) | (1) | 0.33 |
| Preservatives | | q.s. |
| Water, Demineralised | | 20.00 |
| C | | |
| Tris(hydroxymethyl)aminomethane (Art. No. 8386) | (1) | 1.20 |
| Water, Dem. | | 10.00 |
| D | | |
| Pemulen TR-1 | (6) | 0.60 |
| Water, Dem. | | to 100.00 |

Preparation:

For phase D, homogeneously disperse the Pemulen TR-1 in the water and add the pre-dissolved phase C with stirring. For neutralisation of Eusolex 232, the tris(hydroxymethyl)aminomethane is dissolved in the water of phase B, and the Eusolex 232 is added with stirring. After complete dissolution, the remaining raw materials of phase B are added. Stir phase B into phase C/D. Dissolve phase A with warming and stir into phase B/C/D. Homogenise.

Notes:

The preservatives used are:

0.05% of propyl 4-hydroxybenzoate (Merck Art. No. 7427)
0.15% of methyl 4-hydroxybenzoate (Merck Art. No. 6757)

Sources of Supply:
(1) Merck KGaA, Darmstadt
(2) BASF, Ludwigshafen
(3) Dow Corning, Düsseldorf
(4) H. Erhard Wagner, Bremen
(5) GAF, Frechen
(6) Goodrich, Neuss Example 3

Preparation of a sunscreen lotion (W/O) with UV-A/B protection

| | | % |
|---|---|---|
| A | | |
| 2-[4[(Ethyl)phenyl]-1H-imidazo[4,5-b]quinoxaline | (1) | 1.00 |
| Eusolex 2292 (Art. No. 1.05382) | (1) | 3.00 |
| Eusolex 4360 (Art. No. 1.05376) | (1) | 2.00 |
| (Benzophenone-3) | | |
| Dehymuls E | (2) | 6.00 |
| (Dicocoyl Pentaerythrityl Citrate (and) Sorbitan Sesquioleate (and) Cera Alba (and) Aluminium Stearate) | | |
| Arlacel 989 | (3) | 1.00 |
| (PEG-7 Hydrogenated Castor Oil) | | |
| Beeswax (Art. No. 1.11544) | (2) | 2.00 |
| Cetiol J 600 | (2) | 6.00 |
| (Oleyl Erucate) | | |
| Cetiol V | (2) | 6.00 |
| (Decyl Oleate) | | |
| Cetiol OE | (2) | 5.00 |
| (Dicaprylyl Ether) | | |
| Dow Corning 200 (100 cs) | (4) | 1.00 |
| (Dimethicone) | | |
| B | | |
| Glycerin (about 87%) (Art. No. 1.04091) | (1) | 5.00 |
| Magnesium Sulfate Heptahydrate (Art. No. 1.05882) | (1) | 1.00 |
| Preservatives | | q.s. |
| Water, Dem. to | | 100.00 |

Preparation:

Heat phase B to 80° C. and phase A to 75° C. Stir phase B slowly into phase A. Homogenise and cool with stirring.

Notes:

The preservatives used are:

0.05% of propyl 4-hydroxybenzoate (Art. No. 1.07427)
0.15% of methyl 4-hydroxybenzoate (Art. No. 1.06757)

Sources of supply:
(1) Merck KGaA, Darmstadt
(2) Henkel KGaA, Düsseldorf
(3) ICI, Essen
(4) Dow Corning, Düsseldorf Example 4

Preparation of a sunscreen lotion with IR3535™

| | | % |
|---|---|---|
| A | | |
| 2-Phenyl-1H-imidazol[4,5-b]quinoxaline | (1) | 3.00 |
| Eusolex 6300 | (1) | 1.00 |
| (4-Methylbenzylidene Camphor) | | |

-continued

| | | % |
|---|---|---|
| 1R3535 ™ (Art. No. 111887) | (1) | 10.00 |
| (Ethyl Butylacetylaminopropionate) | | |
| (-)α-Bisabolol (Art. No. 130170) | (1) | 0.30 |
| Montanov 68 | (2) | 4.00 |
| (Cetearyl Alcohol (and) Cetearyl Glucoside) | | |
| Myritol 312 | (3) | 2.00 |
| (Carprylic/Capric Triglyceride) | | |
| Mirasil CM 5 | (4) | 2.00 |
| (Cyclomethicone) | | |
| Mirasil DM 350 | (4) | 1.00 |
| (Dimethicone) | | |
| B | | |
| Demin. Water | | to 100.00 |
| Glycerin, 87% (Art. No. 104091) | (1) | 3.00 |
| Preservatives | | q.s. |
| C | | |
| Rhodicare | S (4) | 0.50 |
| (Xanthan Gum) | | |

Preparation:

Heat phases A and B separately to 75° C. Slowly add C to B at 75° C. with stirring and stir until a homogeneous mixture has formed. Subsequently add A to B/C with stirring and homogenise. Cool with stirring.

Notes:

The preservatives used are:

0.05% of propyl 4-hydroxybenzoate (Merck KGaA, Art. No. 130173), 0.15% of methyl 4-hydroxybenzoate (Merck KGaA, Art. No. 130174), 0.30% of Germall 115 (ISP, Frechen)

Sources of Supply:
(1) Merck KGaA, Darmstadt
(2) Interorgana, Cologne
(3) Henkel, KGaA, Düsseldorf
(4) Rhodia, Frankfurt Example 5

| | | % |
|---|---|---|
| A | | |
| 2-[4[(Ethyl)phenyl]-1H-imidazo[4,5-b]quinoxaline | (1) | 1.00 |
| Eusolex 6300 | (1) | 1.00 |
| (4-Methylbenzylidene Camphor) | | |
| IR 3535 ™ (Art. No. 111887) | (1) | 15.00 |
| (Ethyl Butylacetylaminopropionate) | | |
| Eusolex 2292 | (1) | 3.00 |
| (Octyl Methoxycinnamate) | | |
| Dow Corning 5225 C | (2) | 12.00 |
| (Cyclomethicone (and) Dimethicone Copolyol) | | |
| Dow Corning 345 | (2) | 5.00 |
| (Cyclomethicone) | | |
| Gilugel Sil 5 | (3) | 12.00 |
| (Cyclomethicone (and) Al/Mg Hydroxide Stearate) | | |
| Solvent ID | (4) | 13.00 |
| (Isododecane) | | |
| Wiconol 14 | (5) | 2.50 |
| (Polyglyceryl-4 Oleate) | | |
| Beeswax, Bleached (Art. No. 111544) | (1) | 1.60 |
| Carnauba Wax | (6) | 0.40 |

-continued

|  | % |
|---|---|
| B | |
| Demin. Water to | 100.00 |
| Propane-1,2-diol (Art. No. 107478) (1) | 2.00 |
| Sodium chloride (Art. No. 106400) (1) | 2.00 |
| Preservatives (1) | q.s. |
| C | |
| Perfume Oil Bariton (10607) (7) | 0.30 |

Preparation:

Heat phase A to 80° C., cool to 30° C. with stirring. Slowly add phase B to phase A with stirring, stir until a homogeneous mixture has formed and homogenise. Add phase C.

Notes:

The preservative used is:
0.20% of Euxyl K400 (Schülke & Mayr, Norderstedt)

Sources of Supply:
(1) Merck KGaA, Darmstadt
(2) Dow Corning, Düsseldorf
(3) Nordmann, Rassmann GmbH&Co, Hamburg
(4) B P, Düsseldorf
(5) Witco Chemical, Frankfurt
(6) Aug. Schmidt Nachfolger, Bremen
(7) Haarmann & Reimer, Holzminden Examples 6–9

The following formulations can be prepared with all quinoxaline derivatives according to the invention.

|  | Substance | INCI | 6 | 7 | 8 | 9 |
|---|---|---|---|---|---|---|
| A | Quinoxaline derivative | — | 2.0 | 2.0 | 2.0 | 2.0 |
|  | Eusolex ® 6300 | 4-METHYLBENZYLIDENE CAMPHOR | 4.0 | — | — | — |
|  | Eusolex ® 2292 | OCTYL METHOXYCINNAMATE, BHT | — | 6.0 | 7.0 | — |
|  | Eusolex ® 9020 | BUTYL METHOXY-DIBENZOYLMETHANE | — | 1.0 | — | — |
|  | Eusolex ® OCR | OCTOCRYLENE | — | — | — | 7.0 |
|  | Hostaphat CG 120 | ISOSTEARYL PHOSPHATE | 3.00 | 3.00 | 3.00 | 3.00 |
|  | Cetiol SN | CETEARYL ISONONANOATE | 5.00 | 4.00 | 4.00 | 4.00 |
|  | Cetiol OE | DICAPRYL ETHER | 5.00 | 4.00 | 4.00 | 4.00 |
|  | Cetiol 868 | OCTYL STEARATE | 5.00 | 4.00 | 4.00 | 4.00 |
|  | Carbopol Ultrez 10 | CARBOMER | 0.15 | 0.15 | 0.15 | 0.15 |
|  | Propyl 4-hydroxy-benzoate | PROPYLPARABEN | 0.05 | 0.05 | 0.05 | 0.05 |
| B | Glycerol (about 87%) | GLYCERIN | 5.00 | 5.00 | 5.00 | 5.00 |
|  | Tris(hydroxymethyl)amino-methane | TROMETHAMINE | 0.15 | 0.15 | 0.15 | 0.15 |
|  | RonaCare ® Allantoin | ALLANTOIN | 0.30 | 0.30 | 0.30 | 0.30 |
|  | Methyl 4-hydroxy-benzoate | METHYLPARABEN | 0.15 | 0.15 | 0.15 | 0.15 |
|  | Water, demin. | AQUA (WATER) | to 100 | to 100 | to 100 | to 100 |

INCI = International Nomenclature for Cosmetic Ingredients

The working examples shown here confirm by way of example the feasibility of the claimed invention, it being possible to carry out the present invention in the entire range claimed.

The invention claimed is:

1. A method for protecting skin and/or hair of a human from ultraviolet radiation comprising applying onto said skin and/or hair an effective amount of a compound of formula I, which is reproduced as formulae Ia and Ib,

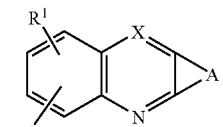

Ia

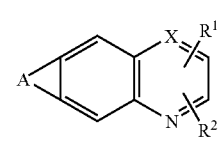

Ib in which
X is an N atom or a C—R$^3$ group
A is a group of formula II or III

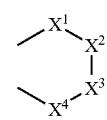

II

-continued

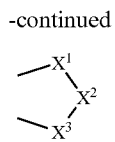
III

X$^1$, X$^2$, X$^3$ and X$^4$ are each, independently of another, =N—, —NR$^4$—, —CR$^5$R$^6$—, —C(=O)— or a =CR— group, with the proviso that, in formula II, from one to 3 of the X$^1$–X$^4$ groups are selected from =N— and —NR$^4$— and that, in formula III, one or two of the X$^1$–X$^3$ groups are selected from =N— and —NR$^4$—, R, R$^1$, R$^2$ and R$^3$ are each, independently of one another, H, alkyl, alkoxy, alkenyl or alkynyl, each having up to 20 carbon atoms, cycloalkyl, cycloalkoxy, cycloalkenyl or bicyclic systems, each having up to 10 carbon atoms, where, in all of these groups, one or more hydrogen atoms may also be substituted by Sub$^1$ and/or one or two CH$_2$ groups may be replaced by C=O, and the cyclic systems may contain 1 to 3 heteroatoms, Hal, OH, NO$_2$, —(CR$^5$R$^6$)$_n$—NR$^5$R$^6$, —(CR$^5$R$^6$)$_n$—N=CR$^5$R$^6$, —(CR$^5$R$^6$)$_n$—CR$^5$=NR$^5$, —(CR$^5$R$^6$)$_n$—NHCOR$^5$, —(CR$^5$R$^6$)$_n$—NHCOOR$^5$, —SR$^5$, —SO$_2$—R$^5$, NR$^5$—SO—R$^6$, —SO—R$^5$, water-solubilising substituents, carboxylate, sulfonate or ammonium radicals, COR$^5$, COOR$^5$, CON5R$^6$, CN, O=S(-R$^5$)=O, O=S(—O R$^5$)=O, O=S(—NR$^5$R$^6$)=O, R$^5$OP(—OR$^6$)=O, OAr, —(CR$^5$R$^6$)$_n$—Ar, —Si(alkyl)$_3$, —Si(alkyl)$_2$H, -Het, —NHHet, —OHet or —(CR$^5$R$^6$)n-Het, R$^1$ and R$^2$ together, with carbon atoms to which they are bonded, may jointly form an unsaturated, partially or fully saturated 4-, 5-, 6- or 7-membered ring, which optionally contains one or more heteroatoms, may be further fused and/or may also be monosubstituted or polysubstituted, Sub$^1$ is Hal, hydroxyl, cyano, amino, nitro, C$_1$–C$_4$-alkylamino, C$_1$–C$_4$-dialkylamino, C$_1$–C$_4$-alkyl or C$_1$–C$_4$-alkoxy, COOH or COO-alkyl, Hal is fluorine, chlorine, bromine or iodine, n is 0, 1, 2, 3 or 4, R$^5$ and R$^6$ are each, independently of one another, H, alkyl, alkenyl, alkynyl, each having up to 20 carbon atoms, cycloalkyl, cycloalkenyl, bicyclic systems, each having up to 10 carbon atoms, where these radicals may be up to trisubstituted by Sub$^1$ and/or one or two CH$_2$ groups may be replaced by C=O, and the cyclic systems may also contain 1 to 3 heteroatoms, —(CR'R'')$_n$—Ar or —(CR'R'')$_n$-Het, the radicals R$^5$ and R$^6$ may also, with one another, in each case together with carbon atoms to which they are bonded, jointly form an unsaturated, partially or fully saturated 4-, 5-, 6- or 7-membered ring, which optionally contains one or more heteroatoms, may also be monosubstituted or polysubstituted and/or may be further fused, R' and R'' are each, independently of one another, H or C$_1$–C$_4$-alkyl, in which one or two CH$_2$ groups may also be replaced by C=O, Ar is an unsubstituted or monosubstituted or polysubstituted aromatic ring or fused ring systems having 6 to 18 carbon atoms, in which one or two CH groups may also be replaced by C=O, Het is an unsubstituted or monosubstituted or polysubstituted heteroaromatic ring having 5 to 7 ring members or a fused ring system, where the heteroatoms present are one or more N, S and/or O atoms, and in which one or two CH groups in the α- or β-position to the heteroatoms may also be replaced by C=O, R$^4$ is H, alkyl, alkoxy, alkenyl, alkynyl, each having up to 20 carbon atoms, cycloalkyl, cycloalkoxy, cycloalkenyl, bicyclic systems, each having up to 10 carbon atoms, where these radicals may be up to trisubstituted by Sub$^2$ and/or one or two CH$_2$ groups may be replaced by C=O, and where the cyclic systems may also contain 1 to 3 heteroatoms, Sub$^2$ is Hal, hydroxyl, cyano, amino, nitro, C$_1$–C$_4$-alkyl or C$_1$–C$_4$-alkoxy, COR$^5$, COOR$^5$, OAr, OHet, —(CR$^5$R$^6$)$_n$—Ar or —(CR$^5$R$^6$)$_n$-Het, —(CR$^5$R$^6$)$_n$—NR$^5$R$^6$, CONR$^5$R$^6$, CN, O=S(—R$^5$)=O, O=S(—OR$^5$)=O, O=S(—NR$^5$R$^6$)=O or R$^5$OP(—OR$^6$)=O.

2. A method according to claim 1, wherein the compound of formula I is of formulae IV, V, VI or VII

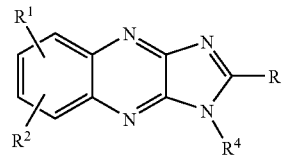
IV

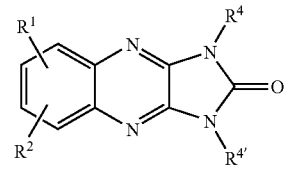
V

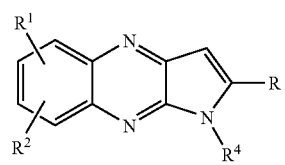
VI

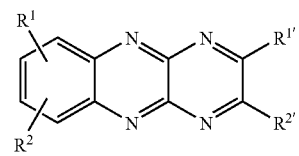
VII in which

R, R$^1$, R$^2$ and R$^4$ are as defined in claim 1,

R$^{1'}$ and R$^{2'}$ are, independently of one another and from R$^1$ and R$^2$, are-defined as R$^1$ in claim 1, and R$^{4'}$ is, independently of R$^4$, is defined as R$^4$ in claim 1.

3. A method according to claim 1, wherein the compound of formula I is of formula VIII

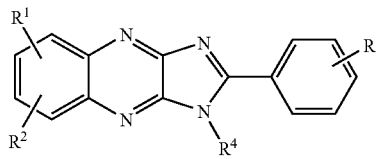
VIII where

R, $R^1$ and $R^2$ are as defined in claim 1, $R^4$ is H or a branched or unbranched $C_{1-20}$-alkyl radical, in which optionally one or more H atoms are replaced by $Sub^2$, $Sub^2$ is as defined in claim 1.

4. A method according to claim 1, wherein the compound of formula I is in a cosmetic or pharmaceutical composition.

5. A method for the photostabilisation of a UV filter comprising bringing into a composition said UV filter and an effective amount of a compound of formula I, which is reproduced as formulae Ia and Ib,

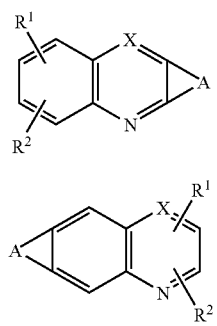

Ia

Ib in which

X is an N atom or a C—$R^3$ group

A is a group of formula II or III

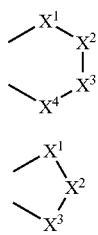

II

III $X^1$, $X^2$, $X^3$ and $X^4$ are each, independently of one another, =N—, —$NR^4$—, —$CR^5R^6$—, —C(=O)— or a =CR— group, with the proviso that, in formula II, from one to 3 of the $X^1$–$X^4$ groups are selected from =N— and —$NR^4$— and that, in formula III, one or two of the $X^1$–$X^3$ groups are selected from =N— and —$NR^4$—, R, $R^1$, $R^2$ and $R^3$ are each, independently of one another, H, alkyl, alkoxy, alkenyl or alkynyl, each having up to 20 carbon atoms, cycloalkyl, cycloalkoxy, cycloalkenyl or bicyclic systems, each having up to 10 carbon atoms, where, in all of these groups, one or more hydrogen atoms may also be substituted by $Sub^1$ and/or one or two $CH_2$ groups may be replaced by C=O, and the cyclic systems may contain 1 to 3 heteroatoms, Hal, OH, $NO_2$, —$(CR^5R^6)_n$—$NR^5R^6$, —$(CR^5R^6)_n$—$N$=$CR^5R^6$, —$(CR^5R^6)_n$—$CR^5$=$NR^5$, —$(CR^5R^6)_n$—$NHCOR^5$, —$(CR^5R^6)_n$—$NHCOOR^5$, —$SR^5$, —$SO_2$—$R^5$, $NR^5$—SO—$R^6$, —SO—$R^5$, water-solubilising substituents, carboxylate, sulfonate or ammonium radicals, $COR^5$, $COOR^5$, $CON^5R^6$, CN, O=S(—$R^5$)=O, O=S(—$OR^5$)=O, O=S(—$NR^5R^6$)=O, $R^5OP$(—$OR^6$)=O, OAr, —$(CR^5R^6)_n$—Ar, —Si(alkyl)$_3$, —Si(alkyl)$_2$H, -Het, —NHHet, —OHet or —$(CR^5R^6)_n$-Het, $R^1$ and $R^2$ together, with carbon atoms to which they are bonded, may jointly form an unsaturated, partially or fully saturated 4-, 5-, 6- or 7-membered ring, which optionally contains one or more heteroatoms, may be further fused and/or may also be monosubstituted or polysubstituted, $Sub^1$ is Hal, hydroxyl, cyano, amino, nitro, $C_1$–$C_4$-alkylamino, $C_1$–$C_4$-dialkylamino, $C_1$–$C_4$-alkyl or $C_1$–$C_4$-alkoxy, COOH or COO-alkyl, Hal is fluorine, chlorine, bromine or iodine, n is 0, 1, 2, 3 or 4, $R^5$ and $R^6$ are each, independently of one another, H, alkyl, alkenyl, alkynyl, each having up to 20 carbon atoms, cycloalkyl, cycloalkenyl, bicyclic systems, each having up to 10 carbon atoms, where these radicals may be up to trisubstituted by $Sub^1$ and/or one or two $CH_2$ groups may be replaced by C=O, and the cyclic systems may also contain 1 to 3 heteroatoms, —$(CR'R'')_n$—Ar or —$(CR'R'')_n$-Het, the radicals $R^5$ and $R^6$ may also, with one another, in each case together with carbon atoms to which they are bonded, jointly form an unsaturated, partially or fully saturated 4-, 5-, 6- or 7-membered ring, which optionally contains one or more heteroatoms, may also be monosubstituted or polysubstituted and/or may be further fused, R' and R" are each, independently of one another, H or $C_1$–$C_4$-alkyl, in which one or two $CH_2$ groups may also be replaced by C=O, Ar is an unsubstituted or monosubstituted or polysubstituted aromatic ring or fused ring systems having 6 to 18 carbon atoms, in which one or two CH groups may also be replaced by C=O, Het is an unsubstituted or monosubstituted or polysubstituted heteroaromatic ring having 5 to 7 ring members or a fused ring system, where the heteroatoms present are one or more N, S and/or O atoms, and in which one or two CH groups in the α- or β-position to the heteroatoms may also be replaced by C=O, $R^4$ is H, alkyl, alkoxy, alkenyl, alkynyl, each having up to 20 carbon atoms, cycloalkyl, cycloalkoxy, cycloalkenyl, bicyclic systems, each having up to 10 carbon atoms, where these radicals may be up to trisubstituted by $Sub^2$ and/or one or two $CH_2$ groups may be replaced by C=O, and where the cyclic systems may also contain 1 to 3 heteroatoms, $Sub^2$ is Hal, hydroxyl, cyano, amino, nitro, $C_1$–$C_4$-alkyl or $C_1$–$C_4$-alkoxy, $COR^5$, $COOR^5$, OAr, OHet, —$(CR^5R^6)_n$—Ar or —$(CR^5R^6)_n$-Het, —$(CR^5R^6)_n$—$NR^5R^6$, $CONR^5R^6$, CN, O=S(—$R^5$)=O, O=S(—$OR^5$)=O, O=S(—$NR^5R^6$)=O or $R^5OP$(—$OR^6$)=O.

6. A method according to claim 4, wherein the cosmetic or pharmaceutical composition comprises one or more antioxidants.

7. A method according to claim 2, wherein $R^1$, $R^2$, $R^{1'}$, $R^{2'}$, $R^{4'}$ and $R^4$ are H, and R is H, methyl, t-butyl or a phenyl ring, which may be monosubstituted or polysubstituted by groups which are as defined in claim 1 for $R^1$.

8. A method according to claim 3, wherein $R^4$ is H, methyl, ethyl or ethyl or ethylhexyl, R is a branched or unbranched $C_{1-20}$-alkyl radical, in which, optionally one or more H atoms are replaced by $Sub^1$, and $Sub^1$ is methyl, ethyl, isopropyl or tertiary-butyl.

9. A method according to claim 5 wherein the UV filter is a dibenzoylmethane derivative.

10. A method according to claim 5 wherein the UV filter is 4-t-butyl-4'-methoxydibenzoylmethane.

11. A method according to claim 1, wherein the compound of formula I is of formulae IV, V, VI or VII

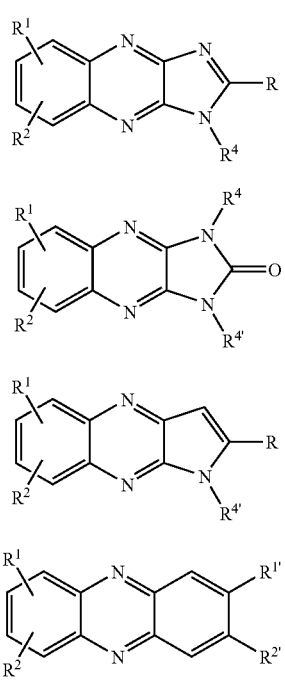

in which

R¹, R², R¹', R²', R⁴' and R⁴ are H,

R is H, methyl, t-butyl or a phenyl ring, which may be monosubstituted or polysubstituted by H, alkyl, alkoxy, alkenyl or alkynyl, each having up to 20 carbon atoms, cycloalkyl, cycloalkoxy, cycloalkenyl or bicyclic systems, each having up to 10 carbon atoms, where, in all of these groups, one or more hydrogen atoms may also be substituted by Sub¹ and/or one or two CH₂ groups may be replaced by C=O, and the cyclic systems may contain 1 to 3 heteroatoms, Hal, OH, NO₂, —(CR⁵R⁶)ₙ—NR⁵R⁶, —(CR⁵R⁶)ₙ—N=CR⁵R⁶, —(CR⁵R⁶)ₙ—CR=NR⁵, —(CR⁵R⁶)ₙ—NHCOR⁵, —(CR⁵R⁶)ₙ—NHCOOR⁵, —SR⁵, —SO₂—R⁵, NR⁵—SO—R⁶, —SO—R⁵, water-solubilising substituents, carboxylate, sulfonate or ammonium radicals, COR⁵, COOR⁵, CON⁵R⁶, CN, O=S(—R⁵)=O, O=S(—OR⁵)=O, O=S(—NR⁵R⁶)=O, R⁵OP(—OR⁶)=O, OAr, —(CR⁵R⁶)ₙ—Ar, —Si(alkyl)₃, —Si(alkyl)₂H, -Het, —NHHet, —OHet or —(CR⁵R⁶)n-Het, Sub¹ is Hal, hydroxyl, cyano, amino, nitro, $C_1$–$C_4$-alkylamino, $C_1$–$C_4$-dialkylamino, $C_1$–$C_4$-alkyl or $C_1$–$C_4$-alkoxy, COOH or COO-alkyl, Hal is fluorine, chlorine, bromine or iodine, n is 0, 1, 2, 3 or 4, R⁵ and R⁶ are each, independently of one another, H, alkyl, alkenyl, alkynyl, each having up to 20 carbon atoms, cycloalkyl, cycloalkenyl, bicyclic systems, each having up to 10 carbon atoms, where these radicals may be up to trisubstituted by Sub¹ and/or one or two CH₂ groups may be replaced by C=O, and the cyclic systems may also contain 1 to 3 heteroatoms, —(CR'R")ₙ—Ar or —(CR'R")ₙ-Het, the radicals R⁵ and R⁶ may also, with one another, in each case together with carbon atoms to which they are bonded, jointly form an unsaturated, partially or fully saturated 4-, 5-, 6- or 7-membered ring, which optionally contains one or more heteroatoms, may also be monosubstituted or polysubstituted and/or may be further fused, R' and R" are each, independently of one another, H or $C_1$–$C_4$-alkyl, in which one or two CH₂ groups may also be replaced by C=O, Ar is an unsubstituted or monosubstituted or polysubstituted aromatic ring or fused ring systems having 6 to 18 carbon atoms, in which one or two CH groups may also be replaced by C=O, Het is an unsubstituted or monosubstituted or polysubstituted heteroaromatic ring having 5 to 7 ring members or a fused ring system, where the heteroatoms present are one or more N, S and/or O atoms, and in which one or two CH groups in the α- or β-position to the heteroatoms may also be replaced by C=O.

12. method for protecting a surface, skin and/or hair from ultraviolet radiation comprising applying onto said surface, skin and/or hair an effective amount of a compound of formula VIII

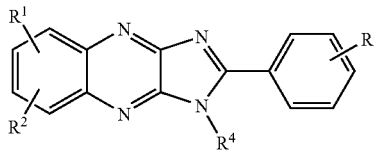

where

R, R¹ and R² are each, independently of one another, H, alkyl, alkoxy, alkenyl or alkynyl, each having up to 20 carbon atoms, cycloalkyl, cycloalkoxy, cycloalkenyl or bicyclic systems, each having up to 10 carbon atoms, where, in all of these groups, one or more hydrogen atoms may also be substituted by Sub¹ and/or one or two CH₂ groups may be replaced by C=O, and the cyclic systems may contain 1 to 3 heteroatoms, Hal, OH, NO₂, —(CR⁵R⁶)ₙ—NR⁵R⁶, —(CR⁵R⁶)ₙ—N=CR⁵R⁶, —(CR⁵R⁶)ₙ—CR⁵=NR⁵, —(CR⁵R⁶)ₙ—NHCOR⁵, —(CR⁵R⁶)ₙ—NHCOOR⁵, —SR⁵, —SO₂—R⁵, NR⁵—SO—R⁶, —SO—R⁵, water-solubilising substituents, carboxylate, sulfonate or ammonium radicals, COR⁵, COOR⁵, CON⁵R⁶, CN, O=S(—R⁵)=O, O=S(—OR⁵)=O, O=S(—NR⁵R⁶)=O, R⁵OP(—OR⁶)=O, OAr, —(CR⁵R⁶)ₙ—Ar, —Si(alkyl)₃, —Si(alkyl)₂H, -Het, —NHHet, —OHet or —(CR⁵R⁶)n-Het, R¹ and R² together, with carbon atoms to which they are bonded, may jointly form an unsaturated, partially or fully saturated 4-, 5-, 6- or 7-membered ring, which optionally contains one or more heteroatoms, may be further fused and/or may also be monosubstituted or polysubstituted, R⁴ is H or a branched or unbranched $C_{1-20}$-alkyl radical, in which optionally one or more H atoms are replaced by Sub², Sub² is Hal, hydroxyl, cyano, amino, nitro, $C_1$–$C_4$-alkyl or $C_1$–$C_4$-alkoxy, COR⁵, COOR⁵, OAr, OHet, —(CR⁵R⁶)ₙ—Ar or —(CR⁵R⁶)ₙ-Het, —(CR⁵R⁶)ₙ—

$NR^5R^6$, $CONR^5R^6$, CN, O=S(—$R^5$)=O, O=S(—$OR^5$)=O, O=S(—$NR^5R^6$)=O or $R^5OP$(—$OR^6$)=O.

13. A method according to claim 12, wherein
$R^4$ is H, methyl, ethyl or ethyl or ethylhexyl,
R is a branched or unbranched $C_{1-20}$-alkyl radical, in which, optionally one or more H atoms are replaced by Sub$^1$, and
Sub$^1$ is methyl, ethyl, isopropyl or tertiary-butyl.

14. A method for protecting a surface, skin and/or hair from ultraviolet radiation comprising applying onto said surface, skin and/or hair an effective amount of a compound of formula I, which is reproduced as formulae Ia and Ib,

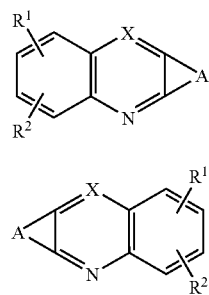

Ia

Ib in which
X is an N atom or a C—$R^3$ group
A is a group of formula II or III

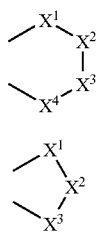

II

III $X^1$, $X^2$, $X^3$ and X4 are each, independently of one another, =N—, —$NR^4$—, —$CR^5R^6$—, —C(=O)— or a =CR— group, with the proviso that, in formula II, from one to 3 of the $X^1$–$X^4$ groups are selected from =N— and —$NR^4$— and that, in formula III, one or two of the $X^1$–$X^3$ groups are selected from =N— and —$NR^4$—, R, $R^1$, $R^2$ and $R^3$ are each, independently of one another, H, alkyl, alkoxy, alkenyl or alkynyl, each having up to 20 carbon atoms, cycloalkyl, cycloalkoxy, cycloalkenyl or bicyclic systems, each having up to 10 carbon atoms, where, in all of these groups, one or more hydrogen atoms may also be substituted by Sub$^1$ and/or one or two CH$_2$ groups may be replaced by C=O, and the cyclic systems may contain 1 to 3 heteroatoms, Hal, OH, NO$_2$, —(CR$^5$R$^6$)$_n$—NR$^5$R$^6$, —(CR$^5$R$^6$)$_n$—N=CR$^5$R$^6$, —(CR$^5$R$^6$)$_n$—CR$^5$=NR$^5$, —(CR$^5$R$^6$)$_n$—NHCOR$^5$, —(CR$^5$R$^6$)$_n$—NHCOOR$^5$, —SR$^5$, —SO$_2$—R$^5$, NR$^5$—SO—R$^6$, —SO—R$^5$, water-solubilising substituents, carboxylate, sulfonate or ammonium radicals, COR$^5$, COOR$^5$, CON$^5$R$^6$, CN, O=S(—R$^5$)=O, O=S(—OR$^5$)=O, O=S(—NR$^5$R$^6$)=O, R$^5$OP(—OR$^6$)=O, OAr, —(CR$^5$R$^6$)$_n$—Ar, —Si(alkyl)$_3$, —Si(alkyl)$_2$H, -Het, —NHHet, —OHet or —(CR$^5$R$^6$)n-Het, $R^1$ and $R^2$ together, with carbon atoms to which they are bonded, may jointly form an unsaturated, partially or fully saturated 4-, 5-, 6- or 7-membered ring, which optionally contains one or more heteroatoms, may be further fused and/or may also be monosubstituted or polysubstituted, Sub$^1$ is Hal, hydroxyl, cyano, amino, nitro, $C_1$–$C_4$-alkylamino, $C_1$–$C_4$-dialkylamino, $C_1$–$C_4$-alkyl or $C_1$–$C_4$-alkoxy, COOH or COO-alkyl, Hal is fluorine, chlorine, bromine or iodine,
n is 0, 1, 2, 3 or 4,
$R^5$ and $R^6$ are each, independently of one another, H, alkyl, alkenyl, alkynyl, each having up to 20 carbon atoms, cycloalkyl, cycloalkenyl, bicyclic systems, each having up to 10 carbon atoms, where these radicals may be up to trisubstituted by Sub$^1$ and/or one or two CH$_2$ groups may be replaced by C=O, and the cyclic systems may also contain 1 to 3 heteroatoms, —(CR'R")$_n$—Ar or —(CR'R")$_n$-Het, the radicals $R^5$ and $R^6$ may also, with one another, in each case together with carbon atoms to which they are bonded, jointly form an unsaturated, partially or fully saturated 4-, 5-, 6- or 7-membered ring, which optionally contains one or more heteroatoms, may also be monosubstituted or polysubstituted and/or may be further fused, R' and R" are each, independently of one another, H or $C_1$–$C_4$-alkyl, in which one or two CH$_2$ groups may also be replaced by C=O, Ar is an unsubstituted or monosubstituted or polysubstituted aromatic ring or fused ring systems having 6 to 18 carbon atoms, in which one or two CH groups may also be replaced by C=O, Het is an unsubstituted or monosubstituted or polysubstituted heteroaromatic ring having 5 to 7 ring members or a fused ring system, where the heteroatoms present are one or more N, S and/or O atoms, and in which one or two CH groups in the α- or β-position to the heteroatoms may also be replaced by C=O, $R^4$ is H, alkyl, alkoxy, alkenyl, alkynyl, each having up to 20 carbon atoms, cycloalkyl, cycloalkoxy, cycloalkenyl, bicyclic systems, each having up to 10 carbon atoms, where these radicals may be up to trisubstituted by Sub$^2$ and/or one or two CH$_2$ groups may be replaced by C=O, and where the cyclic systems may also contain 1 to 3 heteroatoms, Sub$^2$ is Hal, hydroxyl, cyano, amino, nitro, $C_1$–$C_4$-alkyl or $C_1$–$C_4$-alkoxy, COR$^5$, COOR$^5$, OAr, OHt, —(CR$^5$R$^6$)$_n$—Ar or —(CR$^5$R$^6$)$_n$-Het, —(CR$^5$R$^6$)$_n$—NR$^5$R$^6$, CONR$^5$R$^6$, CN, O=S(—R$^5$)=O, O=S(—OR$^5$)=O, O=S(—NR$^5$R$^6$)=O or R$^5$OP(—OR$^6$)=O, wherein the compound of formula I is in a cosmetic or pharmaceutical composition.

15. A method according to claim 14, wherein the cosmetic or pharmaceutical composition comprises one or more antioxidants.

* * * * *

UNITED STATES PATENT AND TRADEMARK OFFICE
CERTIFICATE OF CORRECTION

PATENT NO. : 7,101,537 B2  Page 1 of 2
APPLICATION NO. : 10/471101
DATED : September 5, 2006
INVENTOR(S) : Frank Pfluecker It is certified that error appears in the above-identified patent and that said Letters Patent is hereby corrected as shown below:

On the title page, item (75), Inventors: line 4, reads "Muehital" should read
-- Muehltal --
Column 45, line 29, reads "CON5R$^6$" should read -- CON$^5$R$^6$ --
Column 46, line 53, reads "R$^1$' and R$^2$'" should read -- R$^{1'}$ and R$^{2'}$ --
Column 46, line 55, reads "R$^4$' is," should read -- R$^{4'}$ is, --

Column 49, line 25, reads " 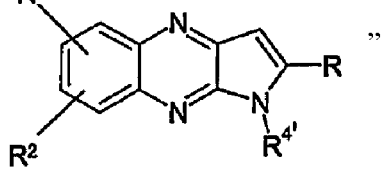 "

should read -- 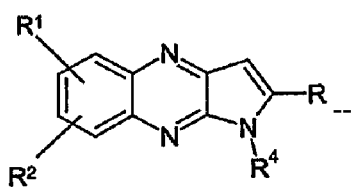 --

Column 49, line 30 reads " 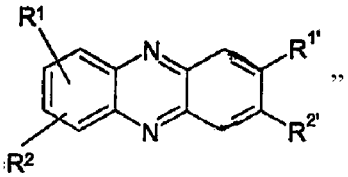 "

should read -- 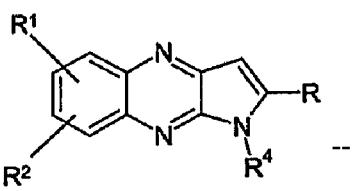 --

UNITED STATES PATENT AND TRADEMARK OFFICE
CERTIFICATE OF CORRECTION

PATENT NO. : 7,101,537 B2
APPLICATION NO. : 10/471101
DATED : September 5, 2006
INVENTOR(S) : Frank Pfluecker It is certified that error appears in the above-identified patent and that said Letters Patent is hereby corrected as shown below:

Column 52, line 54, reads "OHt," should read -- OHet, --

Signed and Sealed this

Seventeenth Day of April, 2007

JON W. DUDAS
*Director of the United States Patent and Trademark Office*